(12) United States Patent
Du

(10) Patent No.: US 11,890,141 B2
(45) Date of Patent: *Feb. 6, 2024

(54) METHOD AND SYSTEM FOR GRAPHICALLY REPRESENTING BLOOD FLOW VELOCITY PARAMETERS

(71) Applicant: Shenzhen Mindray Bio-Medical Electronics Co., Ltd., Shenzhen (CN)

(72) Inventor: Yigang Du, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/723,107

(22) Filed: Apr. 18, 2022

(65) Prior Publication Data

US 2022/0233169 A1    Jul. 28, 2022

Related U.S. Application Data

(63) Continuation of application No. 16/367,514, filed on Mar. 28, 2019, now Pat. No. 11,304,677, which is a
(Continued)

(51) Int. Cl.
*A61B 8/00* (2006.01)
*A61B 8/06* (2006.01)
(Continued)

(52) U.S. Cl.
CPC ............. *A61B 8/463* (2013.01); *A61B 8/06* (2013.01); *A61B 8/145* (2013.01); *A61B 8/465* (2013.01);
(Continued)

(58) Field of Classification Search
CPC ............................... A61B 8/06; A61B 8/5223
See application file for complete search history.

(56) References Cited

U.S. PATENT DOCUMENTS 5,373,848 A * 12/1994 Melton, Jr. .............. A61B 8/06
                                                    600/455
5,623,930 A *  4/1997 Wright .................... A61B 8/06
                                                    600/456
(Continued)

FOREIGN PATENT DOCUMENTS

CN        101297762 A     11/2008
CN        101919711 A     12/2010
(Continued)

*Primary Examiner* — Joel Lamprecht
*Assistant Examiner* — Nyrobi Celestine
(74) *Attorney, Agent, or Firm* — Kory D. Christensen

(57) ABSTRACT

An ultrasonic blood flow parameter displaying method, comprises: acquiring, by means of a probe, an ultrasonic signal from an object to be scanned; acquiring, according to the ultrasonic signal, a plurality of velocities and directions of blood flow within the object to be scanned; extracting the plurality of velocities and directions of blood flow; quantifying the dispersion of the plurality of velocities and directions of the blood flow extracted; and displaying the quantization result of the dispersion. The present invention provides a method for quantifying and evaluating the direction of the motion of blood flow, and provides a better perspective of observation for a user.

19 Claims, 14 Drawing Sheets

Related U.S. Application Data continuation of application No. PCT/CN2016/101208, filed on Sep. 30, 2016.

(51) Int. Cl.
*A61B 8/14* (2006.01)
*A61B 8/08* (2006.01)

(52) U.S. Cl.
CPC ............ *A61B 8/469* (2013.01); *A61B 8/5223* (2013.01); *A61B 8/5246* (2013.01); *A61B 8/488* (2013.01)

(56) References Cited

U.S. PATENT DOCUMENTS

| | | | |
|---|---|---|---|
| 5,876,345 | A | 3/1999 | Eaton |
| 5,910,119 | A | 6/1999 | Lin |
| 5,971,927 | A | 10/1999 | Mine |
| 6,610,014 | B1 | 8/2003 | Yamamoto |
| 9,211,109 | B2 | 12/2015 | Sasaki |
| 9,330,461 | B2 | 5/2016 | Zheng |
| 9,451,933 | B2 | 9/2016 | Duffy |
| 10,342,515 | B2 | 7/2019 | Loupas |
| 10,667,790 | B2 | 6/2020 | Chiang |
| 2005/0124885 | A1* | 6/2005 | Abend ................ A61B 8/085 600/443 |
| 2008/0242996 | A1 | 10/2008 | Hall |
| 2008/0269611 | A1 | 10/2008 | Pedrizzetti |
| 2009/0012393 | A1 | 1/2009 | Choi |
| 2009/0069675 | A1 | 3/2009 | Srinivasan |
| 2010/0069757 | A1* | 3/2010 | Yoshikawa ........ A61B 5/02007 600/454 |
| 2011/0196237 | A1 | 8/2011 | Pelissier |
| 2012/0203111 | A1 | 8/2012 | Naga |
| 2012/0216619 | A1* | 8/2012 | Teramura ............... G01M 9/067 73/645 |
| 2012/0289831 | A9* | 11/2012 | Miyama .................. A61B 8/06 600/443 |
| 2013/0172748 | A1 | 7/2013 | Kim |
| 2013/0218014 | A1 | 8/2013 | Shim |
| 2013/0281855 | A1 | 10/2013 | Baba |
| 2014/0343906 | A1 | 11/2014 | Yagi |
| 2015/0094582 | A1* | 4/2015 | Tanaka ..................... A61B 8/06 600/441 |
| 2015/0141832 | A1* | 5/2015 | Yu .......................... A61B 8/488 600/455 |
| 2015/0297172 | A1* | 10/2015 | Takagi .................. A61B 8/085 600/443 |
| 2016/0157829 | A1 | 6/2016 | Lee |
| 2016/0166236 | A1 | 6/2016 | Hyun |
| 2016/0249883 | A1 | 9/2016 | Lee |

FOREIGN PATENT DOCUMENTS

| | | |
|---|---|---|
| CN | 103930037 A | 7/2014 |
| CN | 104207803 A | 12/2014 |
| CN | 105380680 A | 3/2016 |
| JP | 2014036735 A | 2/2014 |
| JP | WO2015129336 A1 | 9/2015 |

\* cited by examiner

METHOD AND SYSTEM FOR GRAPHICALLY REPRESENTING BLOOD FLOW VELOCITY PARAMETERS

CROSS-REFERENCE TO RELATED APPLICATIONS

This application is a continuation of U.S. patent application Ser. No. 16/367,514, filed Mar. 28, 2019, for ULTRASONIC BLOOD FLOW PARAMETER DISPLAYING METHOD, AND ULTRASONIC IMAGING SYSTEM THEREFOR, which is a continuation of Patent Cooperation Treaty (PCT) App. No. PCT/CN2016/101208, filed Sep. 30, 2016, for "ULTRASONIC BLOOD FLOW PARAMETER DISPLAYING METHOD, AND ULTRASONIC IMAGING SYSTEM THEREFOR," both of which are incorporated herein by reference.

TECHNICAL FIELD

The present disclosure relates to blood flow imaging and display techniques in ultrasonic system, particularly to an ultrasonic blood flow parameter displaying method and ultrasonic imaging system thereof.

BACKGROUND

In a medical ultrasonic imaging device, ultrasonic waves are transmitted into an object to be inspected. In color Doppler blood imaging, as in pulse-wave Doppler imaging and continuous-wave Doppler imaging, the images may be obtained utilizing the Doppler Effect between red blood cells and ultrasonic waves. A color Doppler blood imaging device may include a two-dimensional ultrasonic imaging system, a pulse-wave Doppler (one-dimensional Doppler) blood flow analysis system, a continuous-wave Doppler blood flow measurement system and a color Doppler (two-dimensional Doppler) blood flow imaging system. An oscillator generates two orthogonal signals with a phase difference of $\pi/2$. The two signals are multiplied by the Doppler blood flow signals, respectively, and the product is converted into digital signal by an analog-to-digital (A/D) converter. After being filtered by a comb filter in order to remove the low frequency components generated by vascular wall or valve, etc., the converted digital signal is sent to an autocorrelator where autocorrelation is performed thereon. Since each sample includes the Doppler blood flow information generated by multiple red blood cells, the signal obtained by the autocorrelation is a mixed signal of multiple blood flow velocities. The results of the autocorrelation are sent to a velocity calculator and a variance calculator to obtain mean velocities. The mean velocities may be stored in a digital scan converter (DSC) together with the blood flow spectrum information processed by FFT and two-dimensional image information. Thereafter, the blood flow information is pseudo-color coded by a color processor based on the directions and velocity magnitudes of the blood flow and displayed on a color display, thereby achieving the color Doppler blood flow imaging.

Spectral Doppler imaging is used for quantitative diagnosis of heart valve stenosis and arteriosclerotic lesions, etc. The direction of the blood flow may be different at different times in a cardiac cycle. For example, the blood flow of the carotid artery is laminar under normal conditions, but if plaque exists and the arterial stenosis occurs, the blood flow becomes more disordered. Vortex may occur near the stenosis during systole. The degree of vortex is also an important indicator for judging the stenosis rate. Usually, the area of the vortex is used as the judgment index of the vortex degree. However, in traditional color Doppler, the direction of blood flow cannot be measured, and the area of the vortex can only be manually depicted by red and blue colors and related clinical experience. Therefore, errors are easily generated. The degree of vortex needs to be quantitatively calculated to make the diagnosis more reliable.

SUMMARY

Based on the forgoing, it is desired to provide a parameter display method of ultrasonic blood flow and an ultrasonic imaging system thereof for the deficiencies in the prior art, and provide a new method for quantitatively evaluating the direction of blood flow movement, and provide users with more Good observation perspective.

In one embodiment, an ultrasonic blood flow parameter displaying method is provided, which may include: obtaining an ultrasonic signal from a scan target through a probe; obtaining blood flow velocity directions in the scan target according to the ultrasonic signal; extracting multiple blood flow velocity directions; quantifying a dispersion of the extracted multiple blood flow velocity directions; and displaying a quantification result of the dispersion.

In one embodiment, an ultrasonic imaging system is provided, which may include: a probe configured to transmit an ultrasonic beam to a scan target; a receiving circuit and a beam-former configured to receive an echo signal of the ultrasonic beam and perform a beam-forming on the echo signal to obtain an ultrasonic signal; an image processor configured to obtain blood flow velocity directions in the scan target according to the ultrasonic signal, extract multiple blood flow velocity directions and quantify a dispersion of the extracted multiple blood flow velocity directions; and a display configured to display a quantification result of the dispersion.

DETAILED DESCRIPTION

Figure 1:
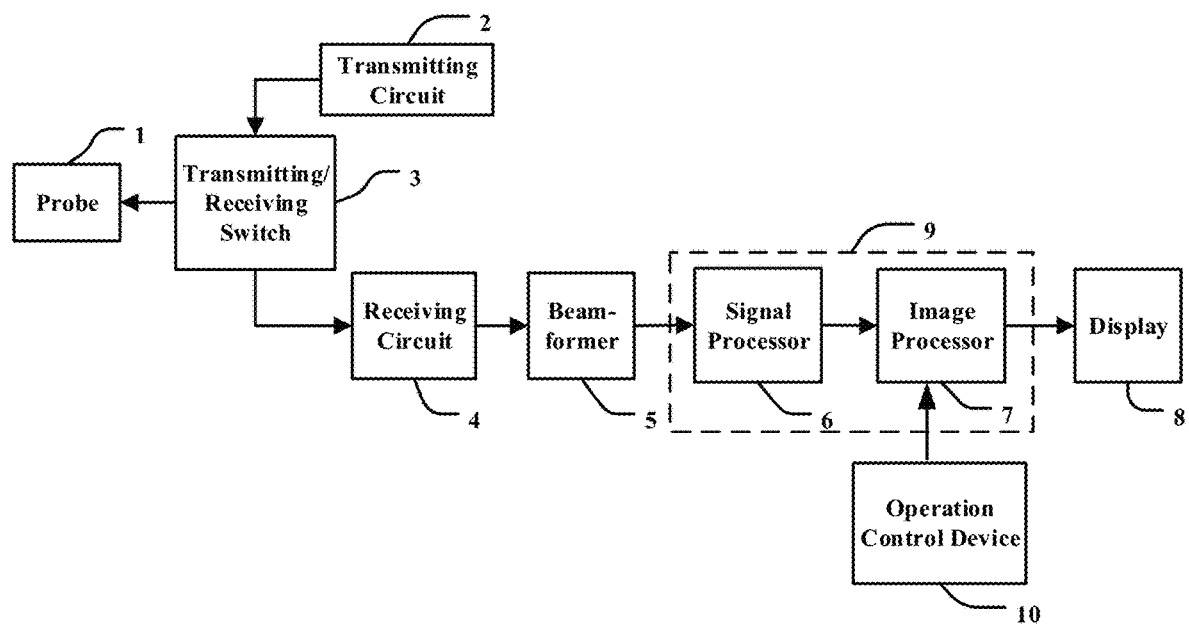
FIG. 1 is a block diagram of an ultrasonic imaging system according to one embodiment of the present disclosure.

FIG. 1 schematically shows a block diagram of an ultrasonic imaging system according to one embodiment of the present disclosure. As shown in FIG. 1, the ultrasonic imaging system may generally include a probe 1, a transmitting circuit 2, a transmitting/receiving switch 3, a receiving circuit 4, a beam-former 5, a signal processor 6, an image processor 7 and a display 8. In the present disclosure, "multiple" may mean two or greater.

In an ultrasonic imaging process, the transmitting circuit 2 may transmit transmitting pulses, which have been delay focused and have certain amplitude and polarity, to the probe 1 through the transmitting/receiving switch 3. The probe 1 may be excited by the transmitting pulses and thereby transmit ultrasonic waves to a scan target (for example, organs, tissues, blood vessels or the like within a human or animal body, not shown), receive ultrasonic echoes which are reflected by a target region and carry information related to the scan target after a certain time interval, and convert the ultrasonic echoes into electric signals. The receiving circuit may receive the electric signals converted by the probe 1 to obtain ultrasonic echo signals and send the ultrasonic echo signals to the beam-former 5. The beam-former 5 may perform processing such as a focus delaying, a weighting and a channel summing, etc. on the ultrasonic echo signals and then send the ultrasonic echo signals to the signal processor 6, where related signal processing procedures will be performed on the ultrasonic echo signals, such as filtering, etc. The ultrasonic echo signals processed by the signal processor 6 may be sent to the image processor 7. The image processor 7 may process the signals in different ways according to the imaging mode desired by the user, so as to obtain image data in different mode. Then, the image data may undergo the processing such as logarithmic compression, dynamic range adjustment and digital scan conversion, etc. to form ultrasonic images of different modes, for example, two-dimensional images such as B images, C images or D images, etc. In addition, the ultrasonic images may also include three-dimensional ultrasonic images. The ultrasonic images formed in the image processor 7 may be sent to the display 8 where they are displayed. In addition, the image processor 7 may further calculate a blood flow velocity vector of the target point within the scan target according to the ultrasonic echo signals, and may add the calculated blood flow velocity vector to the display for display by the rendering process, and/or send the calculated blood flow velocity vector to the display for display. The image processor 7 and the signal processor 6 may be provided separately in different processors or integrated in one single processor 9.

The target point mentioned in this embodiment may be one pixel point on the ultrasonic image or a region block containing at least two pixel points. The blood flow velocity vector of the target point, including the velocity value and the velocity direction, is used to represent the flow velocity information of the blood flow motion state within the scan target. The calculation of the blood flow velocity vector will be explained in detail below.

The probe 1 may generally include an array of multiple transducers. Each time the ultrasonic waves are transmitted, all or a part of the transducers of the probe 1 may be used. In this case, each or each part of the used transducers may be respectively excited by the transmitting pulse and respectively transmit ultrasonic waves. The ultrasonic waves transmitted by the transducers may superpose with each other during the propagation thereof to form a resultant ultrasonic beam transmitted to the scan target. The direction of the resultant ultrasonic beam may be the transmitting angle of ultrasonic waves mentioned in the present disclosure. The used transducers may be simultaneously excited by the transmitting pulses. Alternatively, a certain time delay may exist between the excitation times of the used transducers by the transmitting pulses. By controlling the time delay between the excitation times of the used transducers by the transmitting pulses, the propagation direction (i.e. the transmitting angle) of the resultant ultrasonic beam can be changed, as described in details below.

By controlling the time delay between the excitation times of the used transducers by the transmitting pulses, it may also be possible that the ultrasonic waves transmitted by the used transducers neither focus nor completely diffuse during the propagation thereof, but form a plane wave which is substantially planar as a whole. Alternatively, by controlling the time delay between the excitation times of the used transducers by the transmitting pulses, it may also be possible that the ultrasonic waves transmitted by the transducers are superposed at a predetermined position such that the strength of the ultrasonic waves at the predetermined position is maximum, in other words, such that the ultrasonic waves transmitted by the transducers may be "focused" at the predetermined position. Such predetermined position may be referred to as a "focus". In this case, the obtained resultant ultrasonic beam may be a beam focused at the focus, which may be referred to as a "focused ultrasonic beam" in the present disclosure. During the transmission of the focused ultrasonic beam, the used transducers may work with a predetermined transmission time delay (i.e., a predetermined time delay may exist between the excitation times of the used transducers by the transmitting pulses) and the ultrasonic waves transmitted by the transducers may be focused at the focus to form the focused ultrasonic beam. Alternatively, by controlling the time delay between the excitation times of the used transducers by the transmitting pulses, it may also be possible that the ultrasonic waves transmitted by the used transducers diffuse during the propagation to form a diffused wave which is substantially diffused as a whole. In the present disclosure, such diffused ultrasonic wave may be referred to as a "diffused ultrasonic beam".

Figure 2:
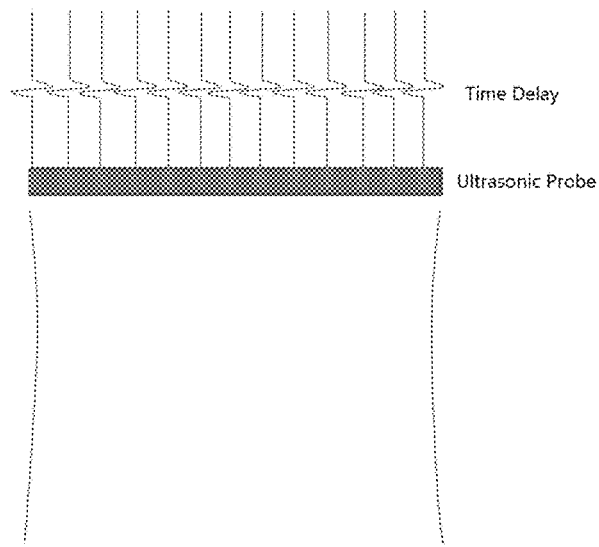
FIG. 2 is a schematic diagram of a vertically transmitted plane ultrasonic beam according to one embodiment of the present disclosure.
Figure 3:
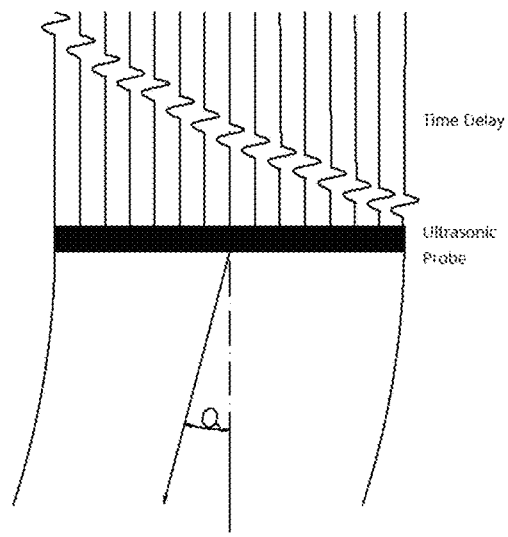
FIG. 3 is a schematic diagram of a steered plane ultrasonic beam according to one embodiment of the present disclosure.

In the case that multiple transducers linearly arranged are excited simultaneously by electronic pulses, the transducers will simultaneously transmit ultrasonic waves and the propagation direction of the resultant ultrasonic beam will be the same as the normal direction of the plane on which the transducers are arranged. For example, for the plane beam vertically transmitted shown in FIG. 2, there is no time delay between the used transducers (i.e. there is no time delay between the excitation times of the transducers by the transmitting pulses) and the transducers are excited simultaneously. The ultrasonic beam formed thereby is a plane beam, i.e. a plane ultrasonic beam. The propagation direction of this plane ultrasonic beam is substantially perpendicular to the surface of the probe 1 from which the ultrasonic waves are transmitted, i.e. the angle between the propagation direction of the resultant ultrasonic beam and the normal direction of the plane on which the transducers are arranged is zero degree. However, in the case that there is time delay between the excitation pulses applied to the transducers, the transducers will successively transmit ultrasonic waves according to the time delay, and there will be an certain angle between the propagation direction of the resultant ultrasonic beam and the normal direction of the plane on which the transducers are arranged. This angle is the transmitting angle of the resultant beam. By changing the time delay, the magnitude of the transmitting angle, and the direction of the transmission in the scanning plane of the resultant beam with respect to the normal direction of the plane on which the transducers are arranged, of the resultant beam may be adjusted. For example, FIG. 3 schematically shows a plane beam with a steered angle. In this case, there is a predetermined time delay between the used transducers (i.e., between the excitation times of the used transducers by the transmitting pulses), and the transducers are excited in a predetermined order by the transmitting pulses. The ultrasonic beam generated thereby is a plane beam, i.e. a plane ultrasonic beam, and there is an angle (for example, the angle $\alpha$ in FIG. 3) between the propagation direction of this plane ultrasonic beam and the normal direction of the plane on which the transducers of the probe 1 are arranged. This angle is the transmitting angle of the plane ultrasonic beam. By changing the time delay, the magnitude of the angle a may be adjusted. Similarly, regardless of the plane ultrasonic beam, the focused ultrasonic beam or the diffused ultrasonic beam, the "transmitting angle" of the resultant beam formed between the direction of the resultant beam and the normal direction of the plane on which the transducers are arranged can be adjusted by adjusting the time delay between the excitation times of the used transducers by the transmitting pulses. The "resultant beam" herein may be the plane ultrasonic beam, the focused ultrasonic beam or the diffused ultrasonic beam mentioned above, etc.

Furthermore, with reference to the foregoing, for a two-dimensional ultrasonic transducer, it can be considered as a combination of multiple linear arrays. Therefore, for the two-dimensional ultrasonic transducer, the "transmitting angle" of the resultant beam formed between the resultant beam and the normal direction of the plane on which the transducers are arranged can also be adjusted by adjusting the time delay between the excitation times of the used transducers by the transmitting pulses.

Figure 4:
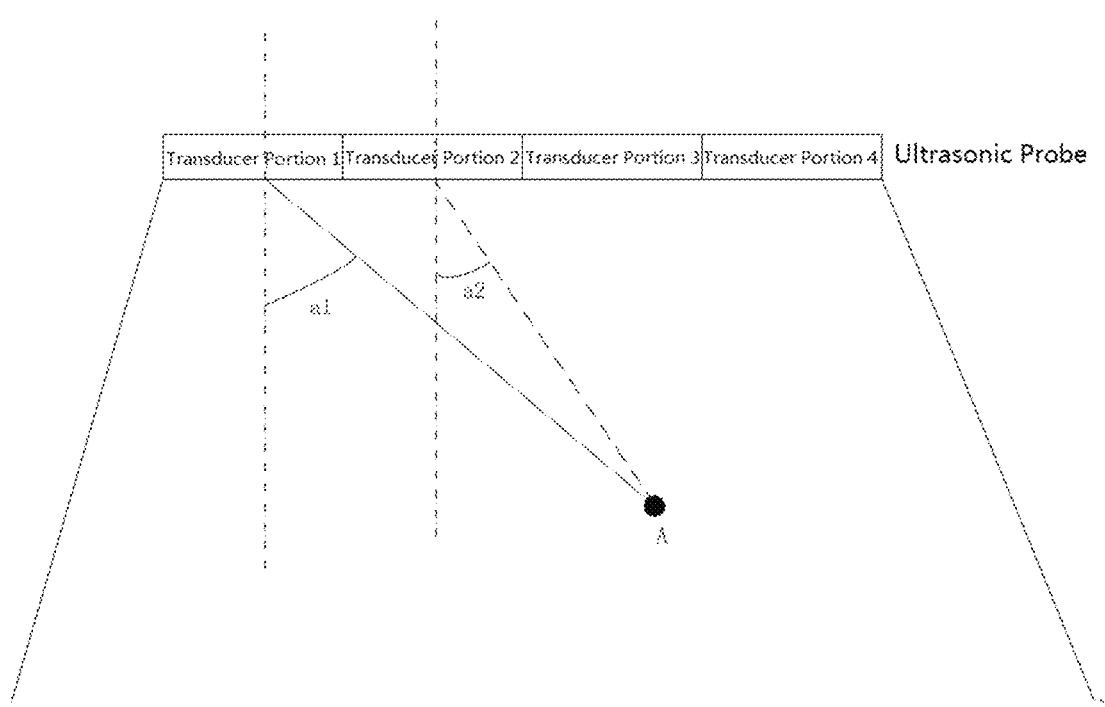
FIG. 4 is a schematic diagram of multi-angle reception in one embodiment of the present disclosure.

Furthermore, by controlling the aperture position of the transducer participating in the reception of the ultrasonic wave (referred to as the receiving transducer herein), the receiving angle of the received ultrasonic signal can be adjusted. For example, as shown in FIG. 4, the ultrasonic probe may include an transducer portion 1, an transducer portion 2, an transducer portion 3 and an transducer portion 4. The transducer portion 1, the transducer portion 2, the transducer portion 3 and the transducer portion 4 may include one transducer or multiple transducers. One or more of the transducer portion 1, the transducer portion 2, the transducer portion 3 and the transducer portion 4 may be used as the receiving element. In FIG. 4, when an ultrasonic beam in a transmitting angle is transmitted to a scan target including the target point position A, the transducer 1 is used as the receiving element, and the ultrasonic beam reflected back from a certain target point position A in the scan target is received. According to the line connecting the aperture position of the element unit 1 and the target point position A (shown as a solid line in FIG. 4), the receiving angle a1 of the echo of the ultrasonic beam received at the current time can be determined. At the same time, the transducer portion 2 may be used as the receiving transducer to receive the echo of the ultrasonic beam reflected from a certain target point position A in the scan target, and the receiving angle a2 of the echo of the ultrasonic beam received at the current time cab be determined according to the line connecting the aperture position of the transducer portion 2 and the target point position A (shown as dotted line in FIG. 4). Two echoes with different receiving angles may be obtained form the echoes of the ultrasonic beam returned from the same target position A. Therefore, the "receiving angle" of the echo of the ultrasonic beam may be defined according to the angle between the line connecting the aperture position of the receiving element and the position of the target point and the normal direction of the plane on which the ultrasonic transducers are arranged. By changing the aperture position of the receiving element in the probe, the "receiving angle" of the echo of the ultrasonic beam can be changed, thereby obtaining ultrasonic signals with different receiving angles returned from the scan target.

Based on the above explanation, when transmitting an ultrasonic beam to the scan target so as to obtain ultrasonic signals in multiple angles from the scan target, the receiving angle of the echo of the ultrasonic beam may be changed by changing the position of the aperture of the receiving element in the probe, thereby obtaining ultrasonic signals corresponding to different receiving angles from the scan target, and alternatively, the transmitting angle of the ultrasonic beam may be changed by controlling the time delay between the excitation time of the transducers participating in the transmission of the ultrasonic waves by the transmitting pulse, thereby obtaining the ultrasonic signals corresponding to different transmitting angles from the scan target. The image processor 7 may calculate the blood flow velocity vectors of multiple target points in the region of interest in the scan target or in the scan target according to the ultrasonic signals in different angles.

In addition, the ultrasonic imaging system shown in FIG. 1 may further include an operation control device 10 for receiving an adjustment signal from an user. The adjustment signal may be used to adjust the imaging parameters such as the transmitting angle of the ultrasonic beam, the receiving angle, and the ultrasonic beam type, etc., or adjust the image of the image processor, the region of interest or the calculation result of the blood flow velocity vector. The operation control device 10 may be a human-computer interaction interface, such as a keyboard, a scroll wheel, a touch gesture receiving and calculating module connected to a touch screen with a touch function, a mouse, a transceiver module for a gesture control signal, and the like. The display 8 in FIG. 1 may include one or more display screens. The display screen in the embodiment may be a touch screen, an LED display screen, or the like.

The image data or the quantification result output by the image processor may also be transmitted to a remote display through a wireless transmission device for display. The solution of the embodiment is not limited to the cart-type ultrasonic device, but may include all devices which are included in a medical internet system and able to display the ultrasonic images.

Figure 5:
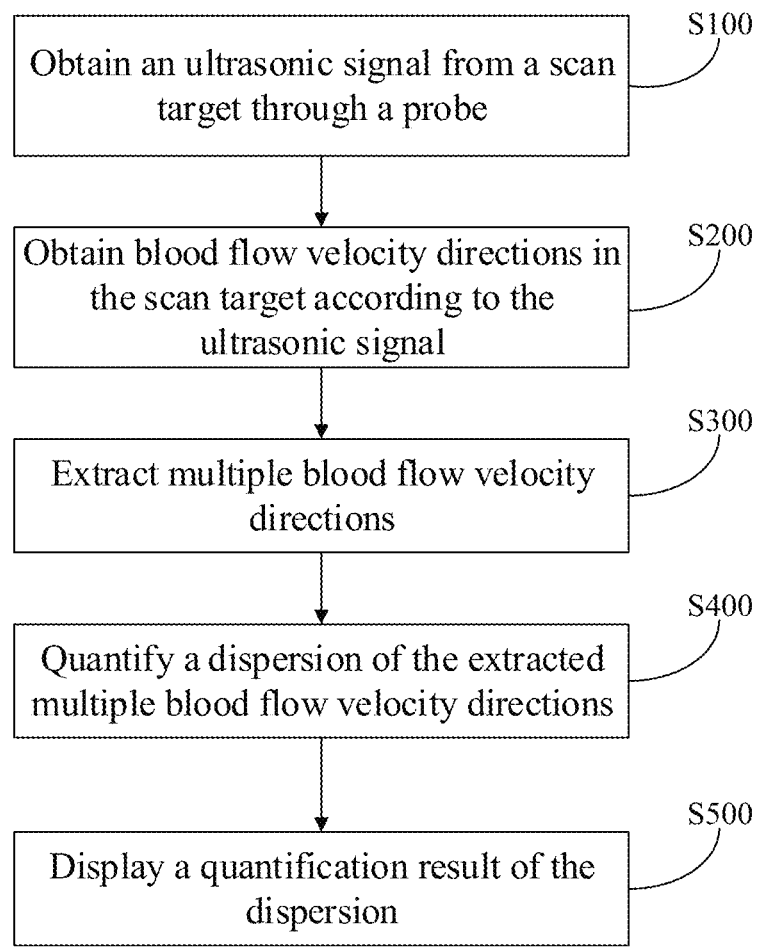
FIG. 5 is a schematic flowchart of a method according to one embodiment of the present disclosure.

FIG. 5 provides a method for displaying the parameter of blood flow, which provides a method for evaluating the degree of vortex or turbulence in blood flow in a blood vessel and can be used as a more intuitive quantitative analysis method for determining the degree of vascular stenosis. The details will be described below.

In step S100 in FIG. 5, the receiving circuit 4 and the beam-former 5 may obtain the received ultrasonic signal from the scan target through the probe 1.

In one embodiment, the probe 1 may be excited by the transmitting circuit 2 to transmit an ultrasonic beam to the scan target, and the echoes of the ultrasonic beam may be received to obtain the ultrasonic signal mentioned in the step S100. The ultrasonic beam transmitted to the scan target in this embodiment may include the focused ultrasonic beam and the unfocused ultrasonic beam. The unfocused ultrasonic beam may include at least one or a combination of the virtual source ultrasonic beam, the non-diffracting ultrasonic beam, the divergent ultrasonic beam and the plane ultrasonic beam, etc. Of course, the embodiments of the present disclosure will not be limited to the types of ultrasonic beams above. It can be seen that the ultrasonic signal in step S100 may be the echo signal of the ultrasonic beam.

In one embodiment, the step S100 may include a step 121 in which a focused ultrasonic beam may be transmitted to the scan target and the echoes of the focused ultrasonic beam may be received to obtain a focused ultrasonic signal which may be used to obtain an ultrasonic image or calculate a blood flow velocity vector, etc. Alternatively, the step S100 may include a step 122 in which a plane ultrasonic beam may be transmitted to the scan target and the echoes of the plane ultrasonic beam may be received to obtain a plane ultrasonic signal which may be used to obtain an ultrasonic image or calculate a blood flow velocity vector, etc. Alternatively, the step S100 may include step 121 and step 122 above, i.e. a focused ultrasonic beam may be transmitted to the scan target to obtain a focused ultrasonic signal and a plane ultrasonic beam may be transmitted to the scan target to obtain a plane ultrasonic signal. The focused ultrasonic signal may be used to obtain at least a portion of the ultrasonic image of the scan target, so as to obtain an ultrasonic image with better quality as a background image, and the plane ultrasonic signal may be used to calculate the blood flow velocity vector in step S200 of FIG. 5.

In the case that two types of beam are transmitted in step S100, the two types of ultrasonic beams may be alternately transmitted to the scan target. For example, the transmission of the focused ultrasonic beam to the scan target may be inserted between the transmissions of the plane ultrasonic beam to the scan target, that is, the steps 121 and 122 above may be alternately performed. This way, the synchronization of the acquisition of the image data of the two types of ultrasonic beams may be ensured, and the accuracy of the blood flow velocity vector obtained by the multi-beam angle transmission may be improved.

In addition to that the beam type is freely selectable, in step S100, the ultrasonic signals in multiple angles may be received for calculating the blood flow velocity vector or obtaining the ultrasonic image. For example, in step S100, ultrasonic beams with different transmitting angles may be transmitted to the scan target, and ultrasonic signals corresponding to the multiple transmitting angles may be received. Alternatively, ultrasonic signals corresponding to different receiving angles may be received from the scan target. Therefore, the ultrasonic signals of multiple angles may correspond to multiple transmitting angles or multiple receiving angles. The details will be described below.

1. For the ultrasonic beams that are transmitted to the scan target in different transmitting angles, the ultrasonic signals of multiple angles may be received along different transmitting angles.

In one embodiment, in step S100, the method may include transmitting ultrasonic beams to the scan target in multiple transmitting angles and receiving the echoes of the ultrasonic beams to obtain the ultrasonic signals corresponding to the multiple transmitting angles as the ultrasonic signals of multiple angles in step S100.

In one embodiment, in step S100, the ultrasonic beams may be transmitted to the scan target in multiple transmitting angles. In this process, the ultrasonic beams in different transmitting angles may be alternately transmitted to the scan target. For example, in the case that the ultrasonic beams will be transmitted to the scan target along two transmitting angles, the ultrasonic beam may be first transmitted to the scan target along the first transmitting angle, and then the ultrasonic beam may be transmitted to the scan target along the second transmitting angle, thereby completing a scanning cycle. Thereafter, the above scanning cycle may be sequentially repeated. Alternatively, all ultrasonic beams in one transmitting angle may be transmitted to the scan target first, and then all ultrasonic beams in another transmitting angle may be transmitted to the scan target, and so on, until the ultrasonic beams in all transmitting angles are transmitted. The different transmitting angles may be obtained by changing the delay time of each transducers or each portion of transducers participating in the ultrasonic transmission, as specifically described with reference to FIG. 2 or FIG. 3.

In one embodiment, multiple ultrasonic beams may be transmitted to the scan target in each transmitting angle to obtain multiple ultrasonic signals which may be used for subsequent processing of the ultrasonic image data. For example, multiple unfocused ultrasonic beams or multiple focused ultrasonic beams may be respectively transmitted to the scan target in multiple transmitting angles. And each time the ultrasonic beam is transmitted, the ultrasonic signal is obtained once.

Alternately transmitting the multiple ultrasonic beams in different transmitting angles to the scan target may enable the calculation of the blood flow velocity vector of the target point substantially at the same moment using the echo data, thereby increasing the accuracy of the calculation of the velocity vector information. For example, in the case that the ultrasonic beams will be transmitted to the scan target for N times respectively in three transmitting angles, the ultrasonic beam may be transmitted to the scan target in a first transmitting angle for at least one time, then the ultrasonic beam may be transmitted to the scan target in a second transmitting angle for at least one time, and then the ultrasonic beam may be transmitted to the scan target in a third transmitting angle for at least one time, thereby completing one scanning cycle. The scanning cycle above may be repeated until all scanning in all transmitting angles are completed. The numbers of the transmission of the ultrasonic beam in different transmitting angles in one scanning cycle may be the same or different. For example, in the case that the ultrasonic beam will be transmitted in two transmitting angles, the transmission sequence may be A1 B1 A2 B2 A3 B3 A4 B4 . . . Ai Bi, and so on, where Ai may be the ith transmission in a first transmitting angle and Bi may be the ith transmission in a second transmitting angle. In the case that the ultrasonic beam will be transmitted in three transmitting angles, the transmission sequence may be A1 B1 B1C1 A2 B2 B2C2 A3 B3 B3C3 . . . Ai Bi Bi Ci, and so on, where Ai may be the ith transmission in a first transmitting angle, Bi may be the ith transmission in a second transmitting angle, and Ci may be the ith transmission in a third transmitting angle.

In addition, in the case that two types of ultrasonic beams will be transmitted to the scan target in step S100, the two types of ultrasonic beams may be transmitted alternately. For example, the step S100 may include a step S101 in which the focused ultrasonic beams may be transmitted to the scan target for multiple times to obtain the image data used for obtaining the ultrasonic images. In step S102, the plane ultrasonic beams may be transmitted to the scan target for multiple times in one or more transmitting angles to obtain the image data to be used for calculating the flow velocity vector information. The transmissions of the focused ultrasonic beams to the scan target may be inserted between the transmissions of the plane ultrasonic beams to the scan target. For example, the multiple transmissions of the focused ultrasonic beam to the scan target may be evenly inserted into the process of step S102 above. Alternatively, it is also possible to employ any of the alternate transmission modes that enable at least a portion of the multiple plane ultrasonic beams transmitted to the scan target to be alternately executed with at least a portion of the multiple focused ultrasonic beams transmitted to the scan target. In this embodiment, the focused ultrasonic beam may be used to obtain an ultrasonic image with better quality, and high real-time velocity vector information may be obtained by using the plane ultrasonic beam due to the high frame rate of plane ultrasonic beam. Furthermore, in order to have better synchronization in data acquisition, the two types of ultrasonic beams may be transmitted alternately.

The receiving circuit 4 and the beam-former 5 may receive the echoes of the transmitted ultrasonic beams and perform beam-forming to obtain the ultrasonic signals. For example, when the echoes of the focused ultrasonic beam are received, the focused ultrasonic signals may be obtained. When the echoes of the plane ultrasonic beam are received, the plane ultrasonic signal may be obtained, and so on. The type of the ultrasonic beam transmitted in step S100 corresponds to the type of ultrasonic signal generated according to the received echoes of such type of ultrasonic beams. For example, the focused ultrasonic beam corresponds to the focused ultrasonic signal, the plane ultrasonic beam corresponds to the plane ultrasonic signal, the divergent ultrasonic beam corresponds to the divergent ultrasonic signal, and the like, which will not be enumerated one by one here.

When the receiving circuit 4 and the beam-former 5 receive the echoes of the ultrasonic beam transmitted in the above step S100, each or each portion of the transducers participating in the transmission of the ultrasonic beam may be used to receive the echoes of the ultrasonic beam transmitted in step S100. Alternatively, the transducers in the probe may be divided into receiving portion and transmitting portion, and each of each portion of the receiving portion may be used to receive the echoes of the ultrasonic beam transmitted in step S100.

When the ultrasonic beam is transmitted in one transmitting angle in step S100, the echoes of the ultrasonic beam in such transmitting angle may be received to correspondingly obtain a group of ultrasonic signals. When the ultrasonic beams are transmitted in multiple transmitting angles in step S100, the echoes of the ultrasonic beams in the multiple transmitting angles may be received to obtain multiple groups of ultrasonic signals corresponding to the multiple transmitting angles. Based on the different transmitting angles, multiple groups of ultrasonic signals corresponding to the different transmitting angles may be received. Further, one group of ultrasonic signals may include multiple ultrasonic signals, and the multiple ultrasonic signals may correspond to the multiple received echo signals of the multiple ultrasonic beams transmitted in each transmitting angle, where one transmission of the ultrasonic beam may correspondingly obtain one ultrasonic signals. For example, in step S100, multiple plane ultrasonic beams may be respectively transmitted to the scan target in multiple different transmitting angles, and then echoes of the plane ultrasonic beams corresponding to the multiple transmitting angles may be respectively received to obtain multiple groups of plane ultrasonic signals belonging to different transmitting angles, where each group of plane ultrasonic signals may include at least two plane ultrasonic signals and each plane ultrasonic signal may be derived from the echoes of the ultrasonic beam transmitted in one transmitting angle for one time. For another example, in the case that multiple focused ultrasonic beams are transmitted to the scan target in step S100, the echoes of the focused ultrasonic beams may be received to obtain multiple focused ultrasonic signals.

2. Receiving ultrasonic signals of multiple angles from the scan target in different receiving angles.

When the transmitting circuit 2 excites the probe 1 to transmit the ultrasonic beam to the scan target in one or more transmitting angles in step S100, the echoes of the ultrasonic beam from the scan target may be received to obtain the ultrasonic signals in different receiving angles as the ultrasonic signals of different angles obtained in step S100 by adjusting the aperture position of the receiving transducers in the probe, as shown in FIG. 4 and related description. The process of transmitting the ultrasonic beam to the scan target in multiple transmitting angles is described in the foregoing.

For example, in one embodiment, in step S100, when receiving the echoes of the ultrasonic beam from the scan target, the aperture position of the receiving transducers in the probe may be adjusted to the first position for receiving the echoes of the ultrasonic beam transmitted in such transmitting angle to obtain the first group of ultrasonic signals belonging to the first receiving angle; and the aperture of the receiving transducer may be adjusted to the second position for receiving the echoes of the ultrasonic beam transmitted in such transmitting angle to obtain the second group of ultrasonic signals belonging to the second receiving angle. Similarly, multiple groups of ultrasonic signals may be obtained based on different receiving angles.

Referring to the foregoing sequence and rules in multiple transmitting angles, in the process of receiving the ultrasonic signals of multiple angles from the scan target in different receiving angles in the embodiments above, the receiving of the multiple groups of ultrasonic signals may be performed alternately according to the different receiving angles. In one embodiment of the present disclosure, the transmitting circuit 2 may excite the probe 1 to transmit the ultrasonic beam to the scan target, and the echoes of the ultrasonic beam may be received respectively in multiple different receiving angles to obtain multiple groups of ultrasonic signals belonging to different receiving angles, where the echoes of one group of ultrasonic beams may be correspondingly received from the scan target in one receiving angle which may be used for subsequent beam-forming, ultrasonic image data processing and calculation of the blood flow velocity vector. The echoes of the multiple groups of ultrasonic beams may be respectively received from the scan target in multiple receiving angles. For example, in step S100, the plane ultrasonic beams may be transmitted to the scan target, and the echoes of the ultrasonic beams may be received in one receiving angle for multiple times to obtain one group of plane ultrasonic signals, where the one group of plane ultrasonic signals may include multiple plane ultrasonic signals. The echoes of multiple groups of plane ultrasonic beams may be received in different receiving angles, thereby obtaining multiple groups of plane ultrasonic signals belonging to different receiving angles.

3. The ultrasonic signal obtained based on one transmitting angle or one receiving angle may also be used to calculate the blood flow velocity vector and/or obtain the ultrasonic image in subsequent steps. For example, in step S100, the plane ultrasonic beam may be transmitted to the scan target in one transmitting angle, and the echoes of the ultrasonic beam may be received in one receiving angle for multiple times to obtain one group of plane ultrasonic signals, where said one group of plane ultrasonic signals may include multiple plane ultrasonic signals. This embodiment can also be suitable for other type of ultrasonic beam above.

Based on the adjustment to the transmitting angle or the receiving angle mentioned above, the ultrasonic signals in one or more angles may be obtained in step S100, where the angle here may include the transmitting angle or the receiving angle. Corresponding to one transmitting angle or receiving angle, one group of ultrasonic signals may be obtained, and therefore multiple groups of ultrasonic signals may be obtained corresponding to different transmitting angles or receiving angles. Each group of ultrasonic signals may include at least one ultrasonic signal obtained in the transmitting angle or the receiving angle. The ultrasonic image of at least a portion of the scan target may be obtained based on any one or two or more of the multiple groups of ultrasonic signals. In addition, based on any one or two or more of the multiple groups of ultrasonic signals, the blood flow velocity vector of the target point in the region of interest may be obtained.

In step S100, in order to facilitate the calculation and improve the image display effect, the ultrasonic signals of multiple angles obtained from the scan target by the probe may belong to different receiving angles or transmitting angles. According to the different angles corresponding to the ultrasonic signals, the ultrasonic signals of multiple angles may be stored as at least one group of data frame set associated with the angle. That is, the obtained one group of ultrasonic signals above may be stored as one group of data frame set associated with the angle, and the data frame set may include at least one frame of image data.

Figure 12:
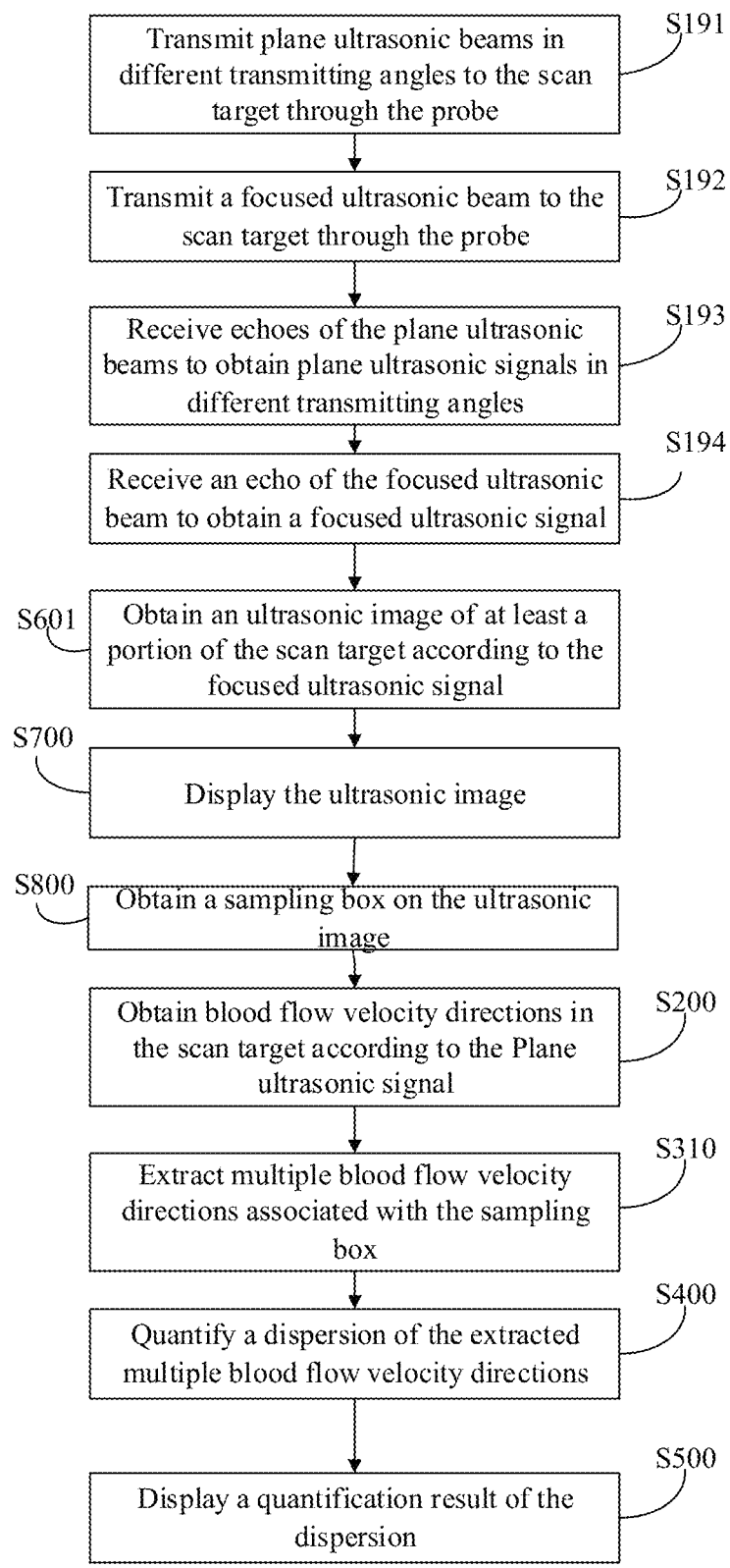
FIG. 12 is a schematic flow chart of a method according to one embodiment of the present disclosure.

FIG. 12 shows a modification based on FIG. 5, in which step S100 may include:

step S191, transmitting the plane ultrasonic beams with different transmitting angles to the scan target through the probe;

step S192, transmitting the focused ultrasonic beams to the scan target through the probe;

step S193, receiving the echoes of the plane ultrasonic beams to obtain the plane ultrasonic signals belonging to different transmitting angles as, or as a part of, the ultrasonic signals obtained in step S100, which may be used to calculate the blood flow velocity vector in step S200, so as to increase the calculation speed of the blood flow velocity vector;

step S194, receiving the echoes of the focused ultrasonic beams to obtain the focused ultrasonic signals as, or as a part of, the ultrasonic signals obtained in step S100, which may be used to obtain the ultrasonic image of at least a part of the scan target in step S601. The ultrasonic image obtained in this embodiment may have better quality.

In step S200 in FIG. 5, the image processor 7 may obtain the direction of the blood flow velocity within the scan target according to the ultrasonic signals obtained in step S100.

In step S200, the directions of the blood flow velocities corresponding to all target points in the entire imaging region of the scan target may be first calculated, and then the directions of the blood flow velocities at multiple target points may be selected. Alternatively, multiple target points at which the directions of the blood flow velocity are desired to be obtained may be first determined, and thereafter, the ultrasonic image may be obtained to calculate the blood flow velocity directions at the multiple target points. The target point in step S200 may be a pixel point or a pixel area input by the user in the region of interest, or may be multiple discrete pixel points or pixel regions automatically generated by the imaging system in the region of interest, which may be used for determining association points for calculating the blood flow velocity direction or blood flow velocity vector at a certain coordinate or at coordinates of a certain image block.

Before obtaining the blood flow velocity direction, the blood flow velocity vector at the multiple target points in the scan target may be obtained according to the ultrasonic signal. The blood flow velocity vector may include the blood flow velocity value and the blood flow velocity direction. Thereafter, the blood flow velocity directions at the multiple target points may be extracted. Alternatively, it is also possible that the blood flow velocity directions are calculated directly without calculating the blood flow velocity values.

In addition, based on the subsequent display manner of the blood flow velocity vector on the ultrasonic image, the target points mentioned in step S200 may be the actual positions selected, or may be the positions calculated according to the blood flow velocity vector calculated at the previous time. For details, reference may be made to the following descriptions about the first display mode and the second display mode.

Regarding both obtaining the blood flow velocity direction and obtaining the blood flow velocity value, reference may be made to the following methods.

Figure 6:
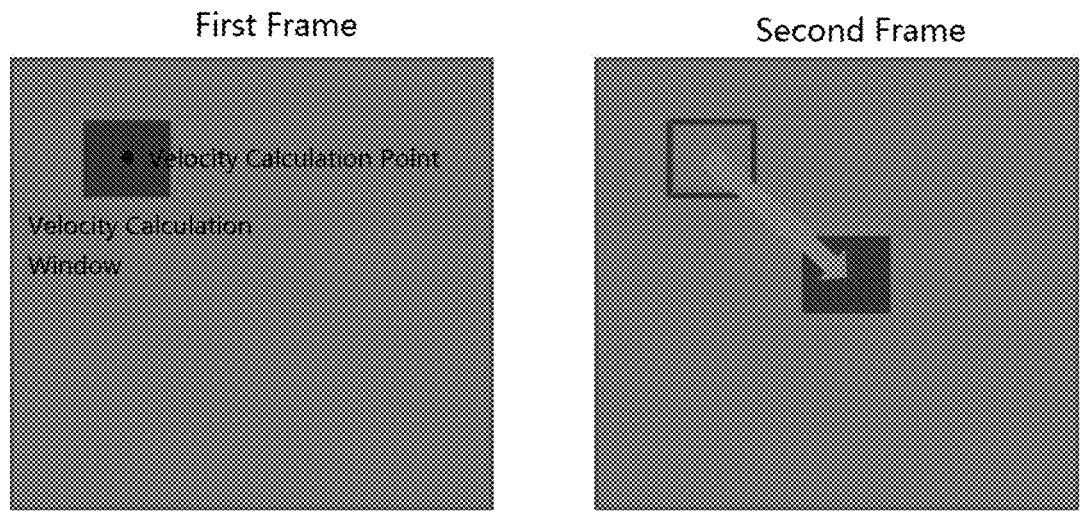
FIG. 6 is a schematic diagram of a calculation method of the blood flow velocity vector according to one embodiment of the present disclosure.

In the first method, the blood flow velocity vector may be calculated based on speckle tracking which utilizing the displacement of the same speckle between two adjacent image frames. Specifically, it is shown in FIG. 6.

First, the ultrasonic signals may be obtained as described above, and the ultrasonic signals may include at least one group of ultrasonic signals.

Secondly, at least two frames of ultrasonic image may be obtained according to the ultrasonic signal. For example, at least a first frame of ultrasonic image (e.g., the largest box on the left in FIG. 6) and a second frame of ultrasonic image (e.g., the largest box on the right in FIG. 6) may be obtained. As described above, in this embodiment, the plane ultrasonic signals may be used to obtain the ultrasonic images for calculating the blood flow velocity vectors of the target points. The plane ultrasonic beam propagates substantially in the entire imaging region. Therefore, generally, one plane ultrasonic signal obtained by transmitting the plane ultrasonic beam one time may be processed to obtain one frame of plane beam echo image data. Herein, the ultrasonic image data of the scan target obtained by processing the plane beam echo signal of the plane ultrasonic beam is referred to as a "plane beam echo image".

Thereafter, a tracking area may be selected in the first frame of ultrasonic image. The tracking area may include the target point at which the velocity vector or velocity direction is desired to be obtained. For example, the tracking area may be a neighborhood of the target point or a data block containing the target point, as shown by the smallest box on the left in FIG. 6.

Next, an area corresponding to the tracking area may be searched for in the second frame of ultrasonic image. For example, an area having the greatest similarity with the tracking area may be searched for as a tracking result area (e.g., the second small box at lower position in the largest square on the right in FIG. 6, where the first small box at top position in the largest square on the right in FIG. 6 represents the position in the second frame of ultrasonic image corresponding to the tracking area). Here, the following formulas may be used to find a similarity matrix, and the area having the greatest similarity with the tracking area may be obtained based on the similarity matrix.

The similarity matrix in the two-dimensional image may be calculated by the following formula (1) or (2).

$$\operatorname*{argmin}_{K,L} \sum_{i=1}^{M} \sum_{j=1}^{N} |X_1(i, j) - X_2(i+K, j+L)| \tag{1}$$

$$\operatorname*{argmin}_{K,L} \frac{\sum_{i=1}^{M} \sum_{j=1}^{N} [X_1(i, j) - \overline{X_1}][X_2(i+K, j+L) - \overline{X_2}]}{\sqrt{\sum_{i=1}^{M} \sum_{j=1}^{N} [X_1(i, j) - \overline{X_1}]^2 \sum_{i=1}^{M} \sum_{j=1}^{N} [X_2(i+K, j+L) - \overline{X_2}]^2}} \tag{2}$$

Where, $X_1$ is the first frame of ultrasonic image, $X_2$ is the second frame of ultrasonic image, i and j are the horizontal and vertical coordinates of the two-dimensional image, $$\operatorname*{argmin}_{K,L}$$

represents the value of K and L when the result of the expression on the right side thereof is minimum, K and L represent a new position in the image, M and N are the sizes of the tracking area in the image, and $\overline{X_1}$ and $\overline{X_2}$ is the average of the tracking area and tracking result area in the first and second frames.

The similarity matrix in the three-dimensional image may be calculated by the following formula (3) or (4).

$$\operatorname*{argmin}_{A,B,C} \sum_{i=1}^{M} \sum_{j=1}^{N} \sum_{k=1}^{L} |X_1(i, j, k) - X_2(i+A, j+B, k+C)| \tag{3}$$

$$\operatorname*{argmin}_{A,B,C} \frac{\sum_{i=1}^{M} \sum_{j=1}^{N} \sum_{k=1}^{L} [X_1(i, j, k) - \overline{X_1}][X_2(i+A, j+B, k+C) - \overline{X_2}]}{\sqrt{\sum_{i=1}^{M} \sum_{j=1}^{N} \sum_{k=1}^{L} [X_1(i, j, k) - \overline{X_1}]^2 \sum_{i=1}^{M} \sum_{j=1}^{N} \sum_{k=1}^{L} [X_2(i, +A, j+B, k+C) - \overline{X_2}]^2}} \tag{4}$$

Where, $X_1$ is the first frame of ultrasonic image, $X_2$ is the second frame of ultrasonic image, i, j and k are the coordinates of the two-dimensional image, $$\operatorname*{argmin}_{A,B,C}$$

represents the value of A, B and C when the result of the expression on the right side thereof is minimum, A, B and C represent a new coordinate position in the image, M, N and L are the sizes of the tracking area in the image, and $\overline{X_1}$ and $\overline{X_2}$ is the average of the tracking area and tracking result area in the first and second frames.

Finally, the velocity vector of the target point may be obtained according to the positions of the tracking area and the tracking result area and the time interval between the first frame of image data and the second frame of image data. For example, the velocity value may obtained by dividing the distance between the tracking area and the tracking result area (i.e., the displacement of the target point within a preset time interval) by the time interval between first frame of plane beam echo image data and the second frame of plane beam echo image data, and the velocity direction may be the direction of the line from the tracking area to the tracking result area, that is, the moving direction of the target point within the preset time interval.

Based on the method above, the blood flow velocity direction in step S200 may be obtained, and the blood flow velocity value may also be obtained. The blood flow velocity vector may be obtained according to the blood flow velocity direction and the blood flow velocity value.

In addition, before calculating the velocity, wall filtering may be performed on the obtained at least two frames of ultrasonic images, that is, wall filtering may be performed on each position in the image in the time direction. The signals representing the tissue in the image change less with time, while signals representing the blood flow change greatly due to the flow of the blood. Therefore, a high-pass filter may be used as the wall filter for the blood flow signals. After the wall filtering, the blood flow signals with higher frequencies may be retained, and the tissue signals with lower frequencies may be filtered out. The wall-filtered signals will have enhanced signal-to-noise ratio.

In the second method, the blood flow velocity vector of the target point may be obtained based on the time gradient and the spatial gradient at the target point, as described below.

First, the ultrasonic signals may be obtained as described above, which may include at least one group of ultrasonic signals. The ultrasonic signals may be in one or more angles. The angle here may be the transmitting angle or the receiving angle. The following embodiment will be described taking the transmitting angle as an example.

Secondly, at least two frames of ultrasonic images may be obtained according to the ultrasonic signals.

Thereafter, a first gradient in the time direction, a second gradient, a second gradient along the transmitting angle and a third gradient along a direction perpendicular to the transmitting angle at the target point may be obtained according to the ultrasonic image, and a fifth velocity component of the target point in the transmitting angle and a sixth velocity component of the target point in the direction perpendicular to the transmitting angle may be calculated according to the first gradient, the second gradient and the third gradient.

Next, the blood flow velocity vector of the target point may be obtained by synthesizing the fifth velocity component and the sixth velocity component. The blood flow velocity vector may include the blood flow velocity value and the resultant angle obtained by the synthesis. The resultant angle may point to the blood flow velocity direction.

In the embodiments above, the transmitting angle is used as an example. In the case that the at least two frames of ultrasonic images are obtained by using the ultrasonic signals obtained in receiving angles as mentioned above, the method described above may also be used, where the "transmitting angle" in the steps will be replaced by "receiving angle". In one embodiment, the plane ultrasonic signals may be used, thereby improving the speed and accuracy of the calculation of the velocity vector. Based on the method above, the blood flow velocity direction in step S200 may be obtained, and the blood flow velocity value may also be obtained. The blood flow velocity vector may be obtained according to the blood flow velocity direction and the blood flow velocity value.

In the third method, the blood flow velocity components in multiple different angles at the target point may be obtained according to the image frame set of different angle. The blood flow velocity vector at the target point may be obtained by synthesizing the blood flow velocity components in the multiple different angles.

In one embodiment, the Doppler imaging technique may be used to calculate the blood flow velocity component at the target point in an angle.

First, the ultrasonic signals may be obtained as described above, which may be in multiple angles. The angle here may be the transmitting angle or the receiving angle. The following embodiment will be described taking transmitting the ultrasonic beams to the scan target in multiple transmitting angles and receiving the echo signals of the ultrasonic beams as the ultrasonic signals in step S100 as an example. In the Doppler ultrasonic imaging method, the ultrasonic beams may be transmitted to the scan target in the same transmitting angle multiple times. The echoes of the multiple ultrasonic beams may be received to obtain multiple ultrasonic signals. Each value of each ultrasonic signal may correspond to a value at a target position when scanning at one transmitting angle.

In step S200, the calculation may be performed as follows.

A Hilbert transform may be performed on the multiple ultrasonic signals in one group of ultrasonic signals corresponding to one transmitting angle along the direction of the transmitting angle to obtain multiple image data which represents the value on each target point by complex number. After N times of transmission and reception, at each target point, there are N complex values that vary with time. Thereafter, the velocity magnitude at the target point z in the direction of the transmitting angle may be calculated according to the following two formulas (5) and (6):

$$v_z = -\frac{c}{4\pi f_0 T_{prf}} \arctan\left(\frac{\Im\{R(1)\}}{\Re\{R(1)\}}\right) \quad \text{formula (5)}$$

$$R(1) = \frac{1}{N-1}\sum_{i=0}^{N-2} x(i)x(i+1) + y(i)y(i+1) + j[y(i+1)x(i) - x(i+1)y(i)] \quad \text{formula (6)}$$

Where Vz is the calculated velocity value in the transmitting angle, c is the speed of sound, $f_0$ is the center frequency of the probe, $T_{prf}$ is the time interval between two transmissions, N is the number of the transmission, x(i) is the real part of the $i^{th}$ transmission, y(i) is the imaginary part of the $i^{th}$ transmission, $\Im$ is the operator for taking the imaginary part, and $\Re$ is operator for taking the real part. The formulas (5) and (6) above are formulas for calculating the velocity values at a fixed position.

Similarly, the velocity value at each target point may be calculated by the N complex values.

In the case that the method above is used to calculate the blood flow velocity components, the Doppler velocity value Vz may be used to represent the blood flow velocity value at the target point along the corresponding transmitting angle, and the transmitting angle may be used to represent the blood flow velocity direction at the target point. The blood flow velocity component along the corresponding transmitting angle may be obtained according to the blood flow velocity value and the blood flow velocity direction. The blood flow velocity component may be expressed in a vector manner.

In the embodiments above, the transmitting angle is used as an example. In the case that the multiple ultrasonic signals obtained in one receiving angle described above are used, the method above may also be used where the transmitting angle is replaced with the receiving angle and the blood flow velocity direction is represented by the receiving angle, thereby the blood flow velocity component along the corresponding receiving angle may be obtained.

With the Doppler method above, according to the ultrasonic signals in different angles, the blood flow velocity values in different angular directions may be respectively obtained, which may be represented by the Doppler frequency.

Generally, in ultrasonic imaging, Doppler processing may be performed on the ultrasonic signal utilizing the Doppler principle to obtain the velocity of the movement of the scan target or the moving portion therein. For example, after the ultrasonic signals are obtained, the velocity of the movement of the scan target or the moving portion therein may be obtained from the ultrasonic signals by the autocorrelation estimation or the cross-correlation estimation. The method for performing the Doppler processing on the ultrasonic signals to obtain the velocity of the movement of the scan target or the moving portion therein may be any method being used currently or to be used in the future in the art which is able to be used to calculate the velocity of the movement of the scan target or the moving portion therein according to the ultrasonic signals, which will not be described in detail here.

Figure 10:
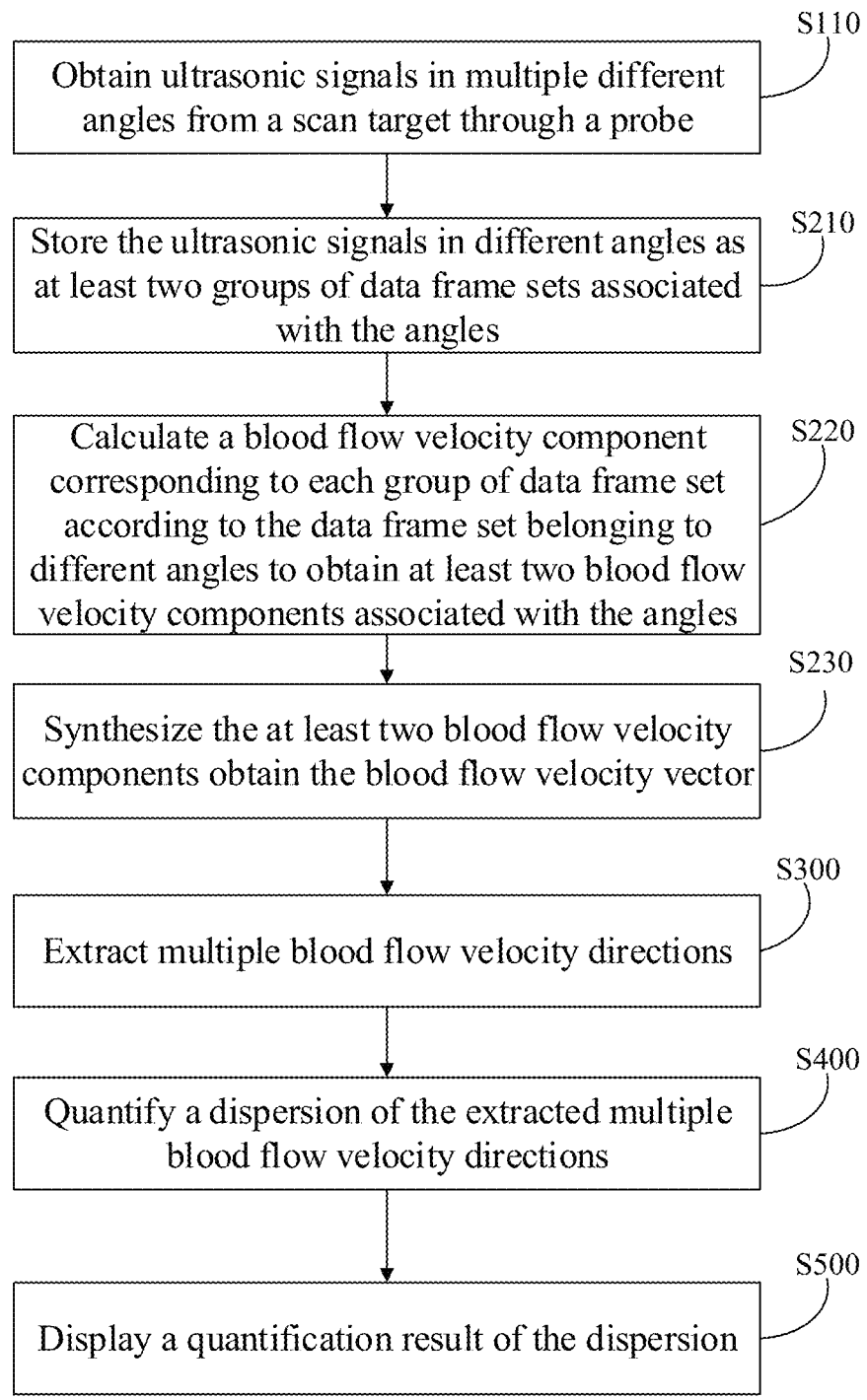
FIG. 10 is a schematic flowchart of a method according to one embodiment of the present disclosure.

According to the method above, the blood flow velocity components at the target point in different transmitting angles or receiving angles may be obtained, and these velocity components may be synthesized at the target point, thereby obtaining the resultant velocity at the target point, that is, the blood flow velocity vector at the target point. As shown in FIG. 10, the details will be described as follows.

First, at least two groups of ultrasonic signals may be obtained as described above. The at least two groups of ultrasonic signals may be in different angles, and the different angles here may include different transmitting angles or different receiving angles (step S110). The ultrasonic signals corresponding to different angles may be stored as at least two groups of data frame sets associated with the angle. In step S210, the ultrasonic signals corresponding to different angles may be stored as at least two groups of data frame sets associated with the angle.

Secondly, based on the data frame set belonging to different angles, the blood flow velocity component corresponding to each group of data frame set may be respectively calculated, as the calculation process above in Doppler imaging techniques, thereby obtaining at least two blood flow velocity components associated with the angles (step S220). At least two blood flow velocity components may be obtained at each target point.

Thereafter, the at least two blood flow velocity components may be synthesized to obtain the blood flow velocity vector desired to be obtained in step S200, which may include the blood flow velocity value and the resultant angle obtained by the synthesis, where the resultant angle points to the blood flow velocity direction (step S230). By this way, the blood flow velocity vectors corresponding to multiple target points may be obtained.

In the embodiment above, the transmitting angle is taken as an example. In the case that the multiple groups of ultrasonic echo signals obtained along multiple receiving angles described above are used, the method above may also be used, but in each step the transmitting angle will be replaced by the "receiving angle".

Regarding the blood flow velocity component corresponding to one transmitting angle or receiving angle, the present disclosure will not be limited to the method above. Other methods known in the art or possible in the future may also be used.

A variety of methods for calculating the blood flow velocity vectors have been proposed in the foregoing. The velocity values in the blood flow velocity vector may include one of the statistics at the target point representing the velocity state, such as the approximate or true velocity, acceleration, velocity variance evaluation values, etc.

In step S120 or alternatively, the following steps may further be included.

The image processor may obtain the ultrasonic image of at least a portion of the scan target according to the ultrasonic signals. The ultrasonic image herein may be a three-dimensional ultrasonic image, or a two-dimensional ultrasonic image, such as a B image, an image in a three-dimensional ultrasonic image database obtained by the scanning body used for display, or an enhanced B image obtained by two-dimensional blood flow display technology. In one embodiment of the present disclosure, the ultrasonic image may be obtained using plane ultrasonic beam or focused ultrasonic beams. However, since the focused ultrasonic beam is more concentrated in each transmission and the image is obtained at the concentration position, the obtained echo signals will have high signal-to-noise ratio, and the obtained ultrasonic image will have better quality. Furthermore, since the focused ultrasonic beam has narrow main lobe and low side lobe, the obtained ultrasonic image will have higher lateral resolution. Therefore, in one embodiment of the present disclosure, the ultrasonic image can be obtained using the focused ultrasonic beams. In order to obtain ultrasonic images with higher quality, multiple focused ultrasonic beams may be transmitted in step S100 to obtain one frame of ultrasonic image.

In one embodiment of the present disclosure, multiple focused ultrasonic beams may be transmitted to the scan target in step S100, and the echoes of the focused ultrasonic beams may be received in step S200 to obtain one group of focused beam echo signals. The ultrasonic image of at least a portion of the scan target may be obtained according to the focused beam echo signals. Using the focused ultrasonic beams, ultrasonic images with high quality may be obtained. Regarding the transmission process combining the plane ultrasonic beam and the focused ultrasonic beam, reference may be made to the description above.

In addition, the data for obtaining the ultrasonic image may be obtained based on any group of ultrasonic signals or any group of data frame set in step S100 above. The ultrasonic image may be displayed by the display, and the sampling box may also be displayed on the ultrasonic image. In this embodiment, there may be one or more sampling boxes, and multiple sampling boxes may overlap. When there are multiple sampling boxes, the quantification results of multiple dispersions may be comparatively observed simultaneously. In one embodiment, the sampling box may be adjusted by the user. Based on the adjustment signal of the user to the sampling box, the sampling box may be redefined to obtain the size and shape of the sampling box.

In step S300, the image processor 7 may extract multiple blood flow velocity directions.

The extracted multiple blood flow velocity directions may include at least one of:

1. the directions of the blood flow velocity at multiple locations at the same time; and 2. multiple blood flow velocity directions corresponding to different times at the same position.

In this embodiment, the same time may include the same time, or the same time period. The time may include at least one real time point, and the time period may include at least one moment.

The moment in this embodiment may also be determined by the frame rate of the image. Using the blood flow velocity directions at multiple positions at the same time, it is possible to evaluate the vortex states at the multiple positions at the same time. Using the blood flow velocity directions corresponding to the same position at different times, it is possible to evaluate the vortex states at the same position in a certain time period. For example, in a cardiac echocardiogram, the extracted multiple blood flow velocity directions may include multiple blood flow velocity directions corresponding to any phase in the same cardiac cycles, so as to evaluate the change in the blood flow direction at the same position in different or same time period in one cardiac cycle. Alternatively, the extracted multiple blood flow velocity directions may include multiple blood flow velocity directions corresponding to the same phase in different cardiac cycles, which may be used to quantitatively evaluate the change in the direction of the blood flow velocity during the systolic or diastolic period. The phase herein may include any moment or time period of time in the cardiac cycle, including systolic and/or diastolic phases.

In this embodiment, the position may be a point or region of interest within the scan target, which may typically be represented as a point or region of interest in at least a portion of the ultrasonic image of the scan target displayed on the display that may be marked or may be displayed. For example, in one embodiment, the position described above may include at least one target point. When a position includes multiple target points, the direction of the blood flow velocity at the position may be the direction of the resultant angle of the blood flow velocity vectors corresponding to the multiple target points at the position, be one of the blood flow velocity directions corresponding to the multiple target points at the position, or be the blood flow velocity direction with the largest number in the blood flow velocity directions corresponding to the multiple target points at the position, etc. Similarly, the blood flow velocity vector at the position may be the resultant velocity of the blood flow velocity vectors corresponding to the multiple target points at the position, be one of the blood flow velocity vectors corresponding to the multiple target points at the position, be the blood flow velocity vector with largest number in the blood flow velocity vectors corresponding to the multiple target points at the position, or be the mean of the blood flow velocity vectors corresponding to the multiple target points at the position, etc.

In one embodiment, the multiple positions where the blood flow velocity directions are to be obtained may be determined according to a set region of interest. The set region of interest may include one of the region of interest selected by the user, the vascular region automatically obtained by the system using image segmentation techniques, the region of interest selected by the system by default and the entire imaging region of the scan target, etc., or any combination thereof. The multiple positions may be multiple discrete or continuous positions in the region of interest, which may be automatically assigned by the system or selected by the user. Therefore, in step S300, multiple blood flow velocity directions in the region of interest may be extracted to quantitatively estimate the region of interest.

In one embodiment, the region of interest may be determined by the sampling box, which may be an area that the system automatically set on the ultrasonic image, the entire imaging area, or an area obtained by the user entering a selection instruction on the ultrasonic image, etc. Generally, the region of interest may include at least one target point, or a neighborhood (data block) containing at least one target point, such as 31 in FIG. 13, 41 in FIG. 14, 51 or A32 in FIG. 15, 61 or 62 in FIG. 16, and 71 or 72 in FIG. 17.

The multiple locations, multiple moments and multiple time periods may be discretely obtained, but not necessarily continuous. The obtained multiple blood flow velocity directions may be a combination of 1 and 2 above. For example, the obtained multiple blood flow velocity directions may include the blood flow velocity directions corresponding to multiple positions at multiple times. In the embodiment above, the flow state of the flow in the vessel may be comprehensively evaluated from the spatial and temporal dimensions.

Figure 11:
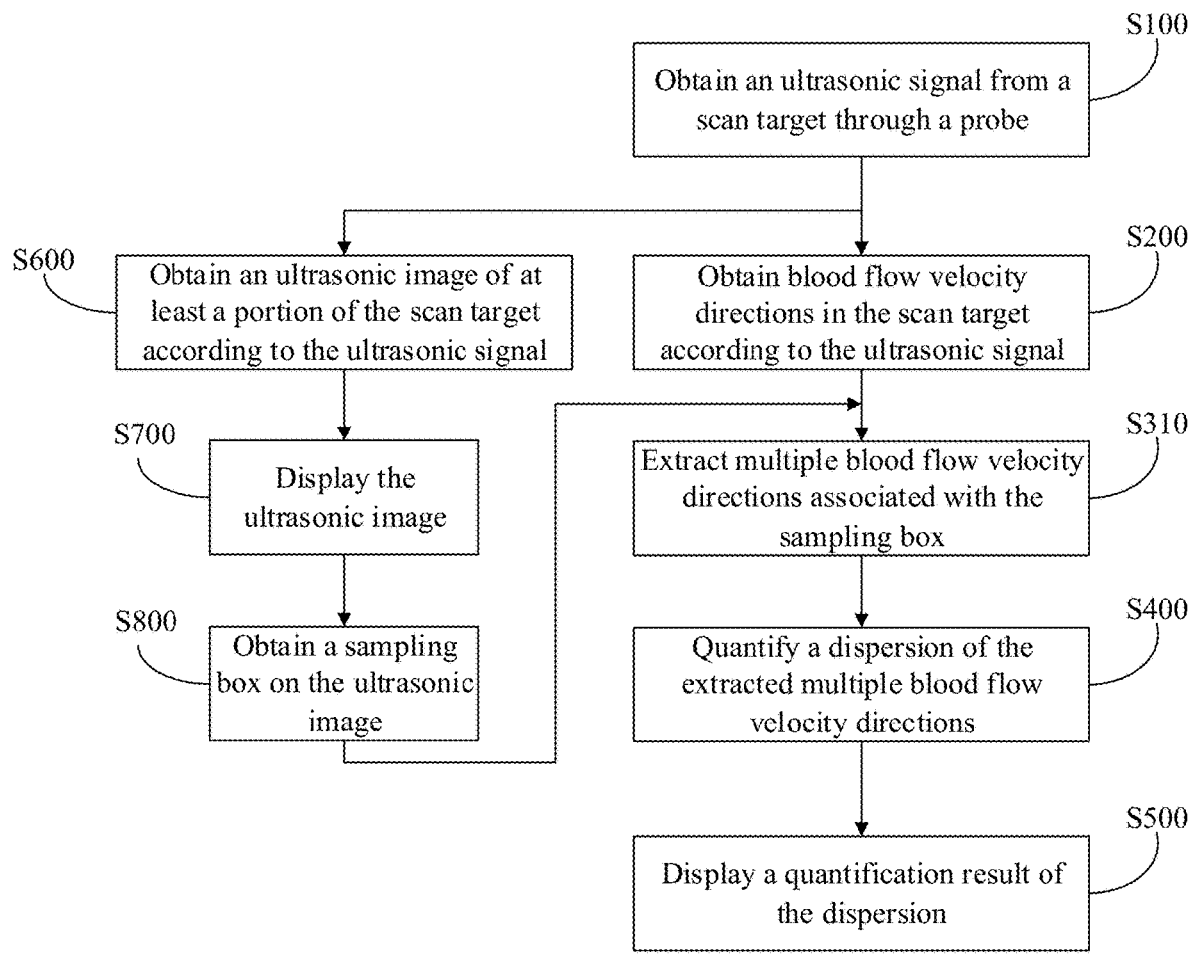
FIG. 11 is a schematic flow chart of a method according to one embodiment of the present disclosure.

In addition, in one embodiment, referring to the modification of FIG. 11 based on that of FIG. 5, the image processor may perform step S600 to obtain the ultrasonic image of at least a portion of the scan target according to the ultrasonic signal, and the display may perform step S700 to display the ultrasonic image. In step S800, the sampling box on the ultrasonic image may be obtained by the operation control device. After the step S200, step S310 may be performed, in which the image processor may obtain multiple blood flow velocity directions associated with the sampling box. The multiple blood flow velocity directions may be the blood flow velocity directions at multiple discrete or continuous positions in the sampling box or the blood flow velocity directions at multiple positions corresponding to the multiple sampling boxes. In one embodiment, the obtained multiple blood flow velocity directions may include at least a portion of the blood flow velocity directions related with positions within the sampling box at the same time and at least a portion of the blood flow velocity directions related with the sampling box and the time. The obtained multiple blood flow velocity directions may be the multiple blood flow velocity directions corresponding to all or a part of the positions in the sampling box. In this way, the part of positions in the sampling box that is desired to be measured may be obtained. These desired positions may be close to or distant from each other, such that the dispersion of the blood flow velocity direction in a relatively large range may be macroscopically analyzed more flexibly.

In the present embodiment, before obtaining the multiple blood flow velocity directions, the method may further includes recording the correspondence relationship between the blood flow velocity vector at each position and time. When obtaining the multiple blood flow velocity directions, the blood flow velocity directions respectively corresponding to the multiple times may be obtained according to the corresponding relationship. This way, the time information about the blood flow velocity direction may be more clearly obtained, which is convenient for display in the subsequent process.

The blood flow velocity direction may be represented by an angle value or a direction vector. For example, the blood flow velocity direction may be represented by an angle value in 0-360 degrees. Alternatively, the blood flow velocity direction may be represented by coordinates in spherical coordinates or Cartesian coordinates.

In step S400, the image processor may quantize the dispersion of the obtained multiple blood flow velocity directions. The dispersion represents the degree of difference between the obtained multiple blood flow velocity directions. Quantization may refer to representing the dispersion with values.

In this embodiment, the dispersion of the obtained multiple blood flow velocity directions may be obtained by one of the following ways:

calculating the variance of the multiple blood flow velocity directions, calculating the extremum of the angle difference of the multiple blood flow velocity directions, and calculating the standard deviation of the multiple blood flow velocity directions. The details of such calculation will be described below.

Figure 7:
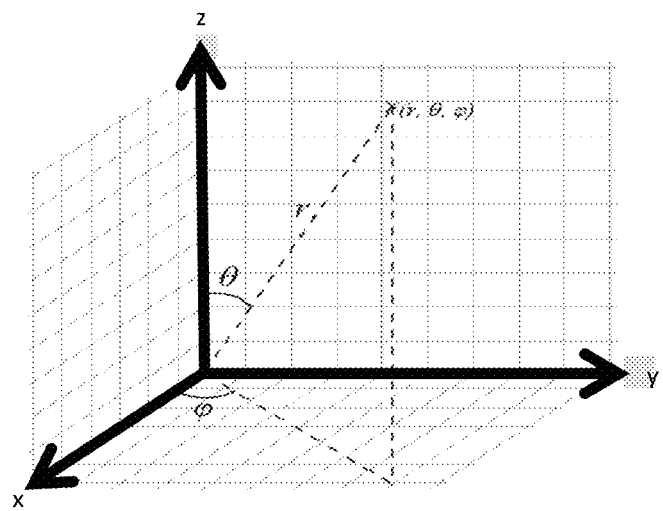
FIG. 7 is a schematic diagram showing the spatial coordinate of the direction of the blood flow velocity in one embodiment of the present disclosure.

Referring to FIG. 7, the calculation of the variance and the standard deviation will be illustrated by way of expressing the blood flow velocity direction in a Cartesian coordinate system.

The conversion formula between the spherical coordinate and the Cartesian coordinate system may be expressed as the following formula (7):

$$x = r \sin \theta \cos \varphi$$

$$y = r \sin \theta \sin \varphi$$

$$z = r \cos \theta \tag{7}$$

The velocity direction of each point in the space may be represented by two angle values, that is, $\theta$ and $\varphi$. The magnitude of the velocity may be represented by r. By coordinate conversion, it may also be represented by a vector in the Cartesian coordinate system, that is, (x, y, z), which includes the magnitude and direction information of the velocity. The dispersion of the velocity direction (angle) at multiple points may be calculated using the following formulas for calculating the vector variance or standard deviation.

The two-dimensional vector of the blood flow velocity vector may be expressed as $(x_1, y_1), (x_2, y_2), \ldots, (x_N, y_N)$. The unit vectors $\vec{e}_1, \vec{e}_2, \ldots \vec{e}_N$, etc. may be obtained by processing, which contain only blood flow velocity direction information. (a, b) represents a two-dimensional unit vector representing the direction of blood flow velocity.

$$\vec{e}_1 = \frac{\vec{r}_1}{|\vec{r}_1|} = \frac{(x_1 \cdot y_1)}{\sqrt{x_1^2 + y_1^2}} = (a_1, b_1) \tag{8}$$

$$\vec{e}_2 = \frac{\vec{r}_2}{|\vec{r}_2|} = \frac{(x_2 \cdot y_2)}{\sqrt{x_2^2 + y_2^2}} = (a_2, b_2)$$

$$\vec{e}_N = \frac{\vec{r}_N}{|\vec{r}_N|} = \frac{(x_N \cdot y_N)}{\sqrt{x_N^2 + y_N^2}} = (a_N, b_N)$$

The average in each dimension may be calculated according to the following formula (9):

$$\bar{a} = \frac{1}{N}\sum_{i=1}^{N} a_i \qquad (9)$$

$$\bar{b} = \frac{1}{N}\sum_{i=1}^{N} b_i$$

The two-dimensional vector variance Var2 used to quantify the dispersion of multiple blood flow velocity directions may be expressed as:

$$\text{Var2} = \frac{1}{N}[(a_1 - \bar{a})^2 + (a_2 - \bar{a})^2 + \qquad (10)$$
$$\cdots + (a_N - \bar{a})^2 + (b_1 - \bar{b})^2 + (b_2 - \bar{b})^2 + \cdots + (b_N - \bar{b})^2]$$

The two-dimensional vector standard deviation SD2 used to quantify the dispersion of multiple blood flow velocity directions may be:

$$\text{SD2} = \sqrt{\text{Var2}} \qquad (11)$$

The three-dimensional vector of the blood flow velocity vector may be $(x_1, y_1, z_1), (x_2, y_2, z_2), \ldots (x_N, y_N, z_N)$.

In the same manner, by processing, unit vectors $\vec{e}_1$, $\vec{e}_2, \ldots \vec{e}_N$ etc. may be obtained, which have only direction information, and (a, b, c) represents a three-dimensional unit vector representing the blood flow velocity direction.

$$\vec{e}_1 = \frac{\vec{r}_1}{|\vec{r}_1|} = \frac{(x_1 \cdot y_1 \cdot z_1)}{\sqrt{x_1^2 + y_1^2 + z_1^2}} = (a_1, b_1, c_1) \qquad (12)$$

$$\vec{e}_2 = \frac{\vec{r}_2}{|\vec{r}_2|} = \frac{(x_2 \cdot y_2 \cdot z_2)}{\sqrt{x_2^2 + y_2^2 + z_2^2}} = (a_2, b_2, c_2)$$

$$\vec{e}_N = \frac{\vec{r}_N}{|\vec{r}_N|} = \frac{(x_N \cdot y_N \cdot z_N)}{\sqrt{x_N^2 + y_N^2 + z_N^2}} = (a_N, b_N, c_N)$$

The average in each dimension may be calculated according to the following formula (13):

$$\bar{a} = \frac{1}{N}\sum_{i=1}^{N} a_i \qquad (13)$$

$$\bar{b} = \frac{1}{N}\sum_{i=1}^{N} b_i$$

$$\bar{c} = \frac{1}{N}\sum_{i=1}^{N} c_i$$

The three-dimensional vector variance Var3 used to quantify the dispersion of multiple blood flow velocity directions may be expressed as:

$$\text{Var3} = \frac{1}{N}[(a_1 - \bar{a})^2 + (a_2 - \bar{a})^2 + \cdots + (a_N - \bar{a})^2 + (b_1 - \bar{b})^2 + \qquad (14)$$
$$(b_2 - \bar{b})^2 + \cdots + (b_N - \bar{b})^2 + (c_1 - \bar{c}) + (c_2 - \bar{c})^2 + \cdots + (c_N - \bar{c})^2]$$

The standard deviation SD3 used to quantify the dispersion of multiple blood flow velocity directions may be:

$$\text{SD3} = \sqrt{\text{Var3}} \qquad (15)$$

In the two-dimensional space, the extremum of the angle difference of the multiple blood flow velocity directions may be obtained in the following manner.

In several angles (assuming N), the angle difference between any two angles may be calculated. The largest angle difference may be obtained, that is, the maximum of the angle difference may be obtained by the formula (16). The smallest angle difference may be obtained, that is, the minimum of the angle difference may be obtained by the formula (17).

$$\max_{\substack{i=1\ldots N \\ j=1\ldots N}} \left\{ 2\arcsin\left|\sin\left(\frac{d_i - d_j}{2}\right)\right| \right\} \qquad (16)$$

$$\min_{\substack{i=1\ldots N \\ j=1\ldots N}} \left\{ 2\arcsin\left|\sin\left(\frac{d_i - d_j}{2}\right)\right| \right\} \qquad (17)$$

Where $d_i$ represents the magnitude of the angle value of the i-th blood flow velocity direction, and $d_j$ represents the magnitude of the angle value of the j-th blood flow velocity direction $d_i$ or $d_j$ is an angle value in 0-360 degrees.

Regardless of the number of angles and the angle, the extremums of the angle difference calculated according to the formulas (16) and (17) above are values varying between 0 and 180 degrees. The larger the value, the larger the extremum of the angle difference.

The extremum of the angle difference of the multiple blood flow velocity directions in two or three dimensions may be calculated in the form of vectors, as shown by the formulas (18) and (19) below.

The angle difference maximum in two-dimensional or three-dimensional space may be calculated as follows:

angle difference maximum= (18)

angle difference minimum= (19)

The angle difference maximum may also be measured by distance, such as the following formulas (20) and (21)

$$\text{angle difference maximum} = \max_{\substack{i=1\ldots N \\ j=1\ldots N}} |\vec{e}_i - \vec{e}_j| \qquad (20)$$

angle difference minimum= (21)

Where $\vec{e}_1, \vec{e}_2 \ldots \vec{e}_N$ are 2D or 3D unit vectors, as defined above. What is obtained is the distance between two vectors (suitable for both two-dimensional and three-dimensional space).

It can be seen that when calculating the angle difference extremum of the multiple blood flow velocity directions, the angle difference between any two angles may be first calculated. Thereafter, the maximum or minimum of the angle differences may be obtained. In the present embodiment, the angle difference may be obtained by the formulas (18) and (19) or the formulas (20) and (21).

In addition, the variance of the multiple blood flow velocity directions may also be calculated using another method.

The blood flow velocity direction may be quantized to a value between 0 and 360 degrees (or −180 to 180 degrees), and the variance Var may be calculated using the following formula (22).

$$C = \sum_{i=1}^{i=N} \cos\theta$$
$$S = \sum_{i=1}^{i=N} \sin\theta$$
$$\text{Var} = \left[1 - \frac{\sqrt{C^2 + S^2}}{N}\right]$$
(22)

In the formula, θ is the quantized angle value of the blood flow velocity direction, and N represents the number of the target points in the sampling box or the number of the positions of different sampling boxes. Var is a number in 0-1. The Var may be multiplied by 100, such that the variance is a number in 0-100. Other modifications of the Var may be similarly obtained. The larger the Var, the greater the change of the velocity direction in the sampling box (the greater the dispersion, the greater the degree of turbulence or vortexs, etc.). The smaller the Var, the higher the consistency of the velocity directions in the sampling box and the closer the flow to laminar flow. For example, when Var is 0, the blood flow velocity directions at all points in the sampling box will be completely the same, which is a typical laminar flow state.

Although several methods have been provided above in this embodiment, the method for quantifying the dispersion of the multiple blood flow velocity directions will not be limited thereto in the present disclosure. Other user-selected methods may also be used. A variety of quantitative methods may be provided in the system for the user to select, and a comparative view of the dispersion obtained by different quantization methods may be provided, so as to achieve comprehensive evaluation.

In step S500, the quantification result of the dispersion may be displayed by the display. The ultrasonic image may also be displayed by the display, and the sampling box may be marked on the ultrasonic image for comparatively observing the quantification results of the dispersions at the associated regions.

In the present embodiment, the quantification result of the dispersion may be displayed by at least one of the following ways:

displaying the quantification result of the dispersion by text;

displaying an icon model constructed based on the quantification result; and superimposing the quantification result of the dispersion on the ultrasonic image.

In one embodiment, superimposing the quantification result of the dispersion on the ultrasonic image may include:

generating a particle block associated with a specific region using the image processor, where the coded color of the particle block is associated with the quantification result of the dispersion of the blood flow velocity directions within the specific region, and displaying the particle block with the coded color at a certain area in the ultrasonic image to obtain a dispersion image. Regarding the particle block, reference may be made to the color spots and the color block A1, A2, A3, and A4 in FIG. 13 and FIG. 14.

In the present embodiment, the specific region may mean that, the quantization results of the blood flow velocity directions in a specific region in the ultrasonic image correspond to one particle block, and the specific region may have a size set by the system or selected by the user, e.g., 3*8, 4*4, 5*5. The ultrasonic image may be segmented according to the size of the specific region, and the quantization results of the dispersion of the blood flow velocity directions in the multiple specific regions in the ultrasonic image may be calculated. The multiple specific regions may be obtained by non-overlapping segmentation to the ultrasonic image. The area size of the specific regions may be the same or different. For example, the ultrasonic image may be 80*80, and may be equally divided into 100 8*8 specific regions which do not overlap with each other. The dispersion of the blood flow velocity directions of each specific region may be calculated according to the blood flow velocity directions at the target points in each specific region. The calculation result may be the quantization result of the dispersion of the center point in the specific region. The specific region may be color-coded according to the magnitude of the quantization result of the dispersion and displayed on the ultrasonic image.

Figure 8:
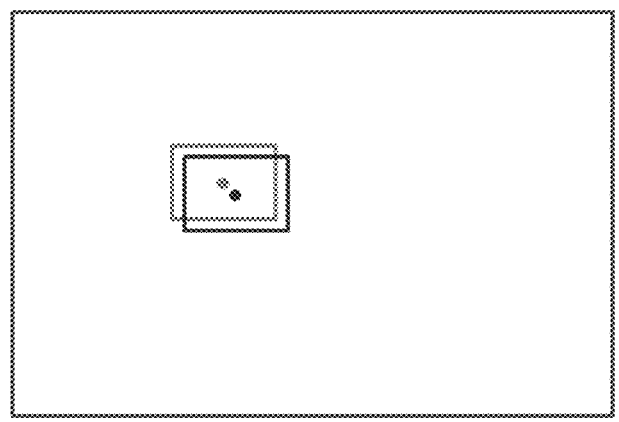
FIG. 8 is a schematic diagram of calculation of the dispersion image in one embodiment of the present disclosure.

The multiple specific regions here may also be obtained by continuous overlapping segmentation to the ultrasonic image. For example, as shown in FIG. 8, a small sampling box (e.g., the small box in FIG. 8) may be moved in the entire sampling box (e.g., the large box in FIG. 8) by a step of one or more pixel points to obtain new image regions, thereby achieving the continuous overlapping segmentation. The multiple image regions obtained by moving the small sampling box may be the multiple specific regions. When calculating the dispersion of the blood flow velocity directions in the entire sampling box in FIG. 8, a small sampling box (e.g., the small box in FIG. 8) may first be selected, and the dispersion of the blood flow velocity directions may be calculated according to the blood flow velocity directions at the target points in the small sampling box, where the calculation result may be the quantization result of the center point of the small sampling box. This small sampling box may be moved and the calculation may be performed again to obtain the dispersion of the blood flow velocity direction at the center position thereof, and so on. This way, the dispersion of the blood flow velocity direction in multiple overlapping specific regions in the large sampling box may be obtained. The size of this small sampling box may be variable, and the distance of the movement after each calculation may also be variable. In FIG. 8, the two overlapping boxes represent the small sampling boxes in two calculations, and the calculated value may be the quantization result of the dispersion at the corresponding center point. According to the magnitude of the quantization results, the small sampling boxes may be color coded and displayed on the ultrasonic image to form the dispersion image. The two sampling boxes can have overlapping portions. The bigger the overlapping portion, the higher the spatial resolution of the calculated dispersion image.

Figure 13:
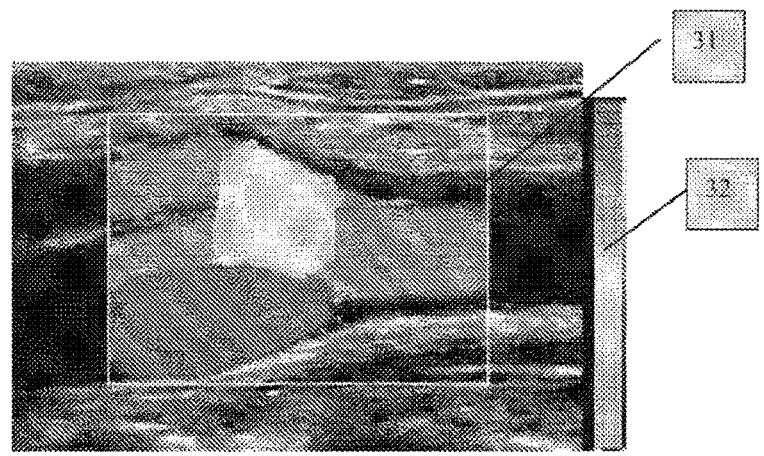
FIG. 13 is a schematic diagram showing a display effect of the dispersion image according to one embodiment of the present disclosure.

FIG. 13 shows a dispersion image with color effect, in which the quantization result of the dispersion of corresponding specific regions are superimposed on the vessel in the sampling box 31 to obtain a dispersion image with multiple color blocks as shown in FIG. 13. Furthermore, a color code bar 32 may be provided on the interface to prompt the user to identify the magnitude of the dispersion.

Figure 14:
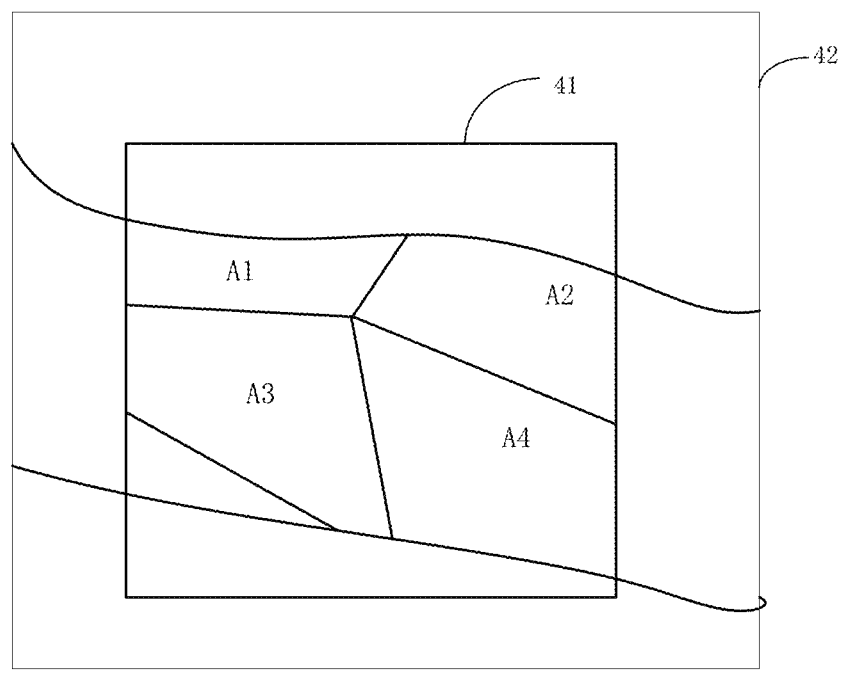
FIG. 14 is a schematic line diagram of FIG. 13.

FIG. 14 is a line diagram of FIG. 13, in which 41 is the sampling box, 42 is the ultrasonic image, and A1, A2, A3 and A4 are respectively displayed with different colors to show the difference in dispersion in the current region. In addition, in the case that the method in FIG. 8 is used, the color blocks A1, A2, A3 and A4 will be further subdivided such that the spatial resolution of the dispersion image may be improved. Therefore, a new displaying method is provided in the present embodiment, which can provide a more intuitive observation angle to the doctor, and exhibit the blood flow movement in the vessel by the superimposed display on the ultrasonic image. In FIG. 13, green indicates the smallest dispersion, and red indicates the largest dispersion.

Figure 16:
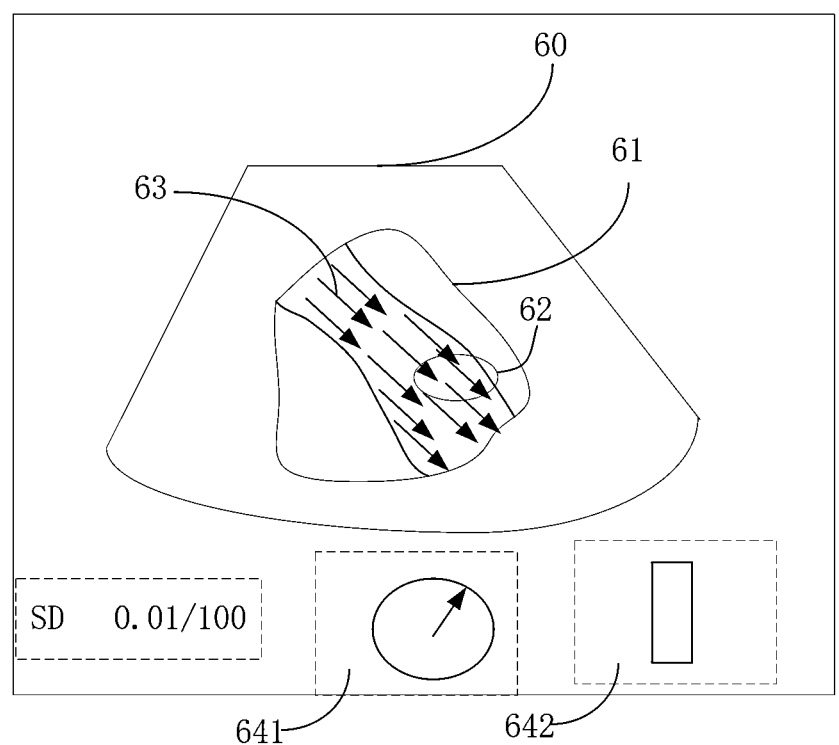
Figure 17:
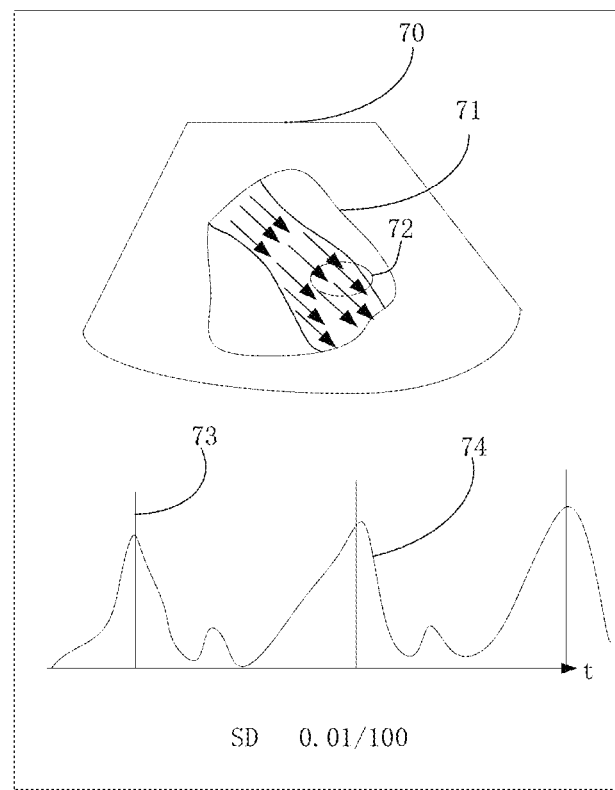

In one embodiment, the quantification result of the dispersion may be displayed directly at any position on the display interface using text, such as "SD 0.01/100" shown in FIG. 16 and FIG. 17.

In one embodiment, the icon model may be constructed based on the quantification results. The icon model may be displayed to show the quantification results of the dispersion associated with the sampling frames. The icon mode may be displayed in many ways. For example, as shown by 642 in FIG. 16, a rectangular column with coded color may be used, and the coded color may be related to the magnitude of the quantization result of the dispersion. Also, as shown by 641 in FIG. 16, a circular icon with an arrow may be used, where the direction of the arrow may be related to the quantification result of the dispersion.

Figure 18:
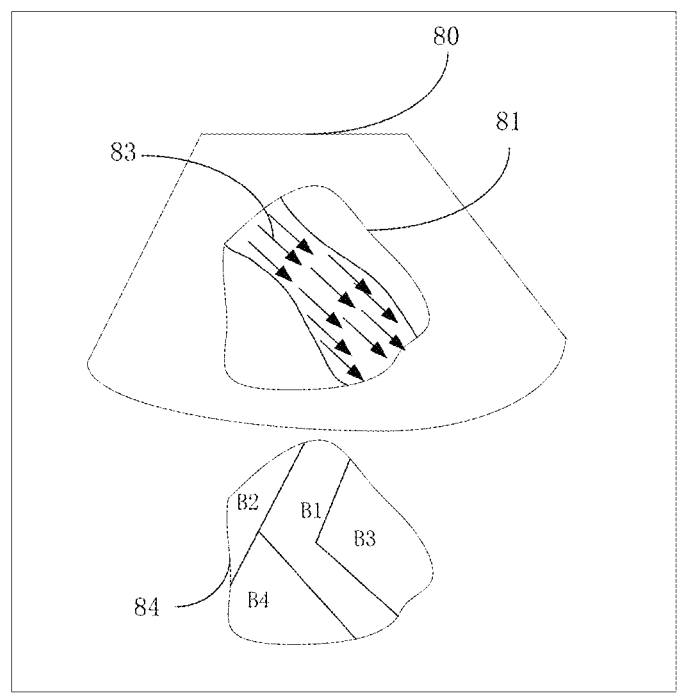

It is also possible to construct the icon model based on the positional relationship. For example, as shown in FIG. 18, the icon modulo 84 corresponding to the image region of the vessel or a part of the vessel may be constructed according to the sampling box 81 in the display area 80 in the ultrasonic image or the identifier 83 representing the blood flow velocity vectors in the region of interest 91. The icon model 84 may be divided into multiple blocks (B1, B2, B3, B4), and the quantification result of dispersion in the region in the ultrasonic image corresponding to each block may be calculated. The quantification results of dispersion may be superimpose on the corresponding blocks in texts or coded colors for presentation on the display.

Figure 15:
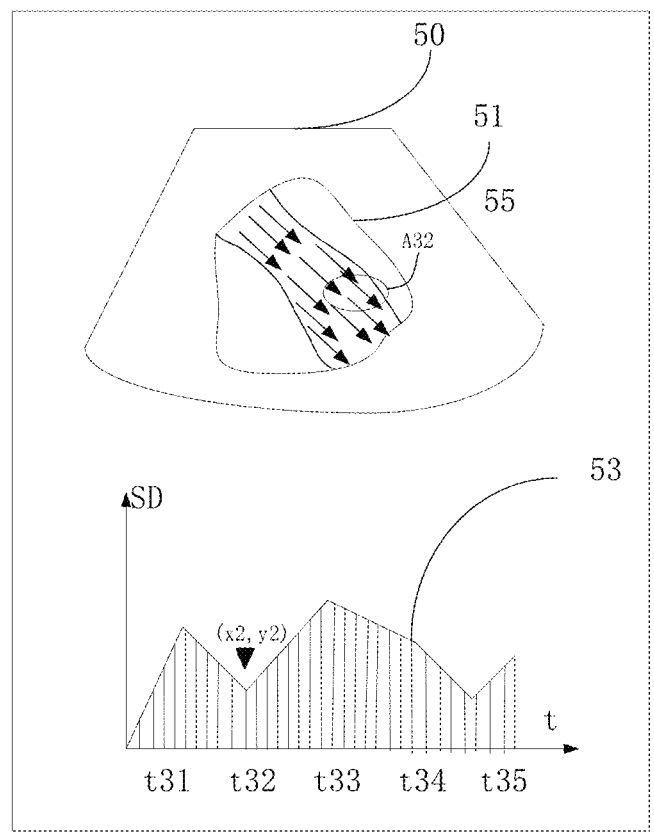
FIG. 15, FIG. 16, FIG. 17, FIG. 18 and FIG. 19 are schematic views comparatively showing the ultrasonic images and the discrete quantized structures in various embodiments of the present disclosure, respectively.
Figure 19:
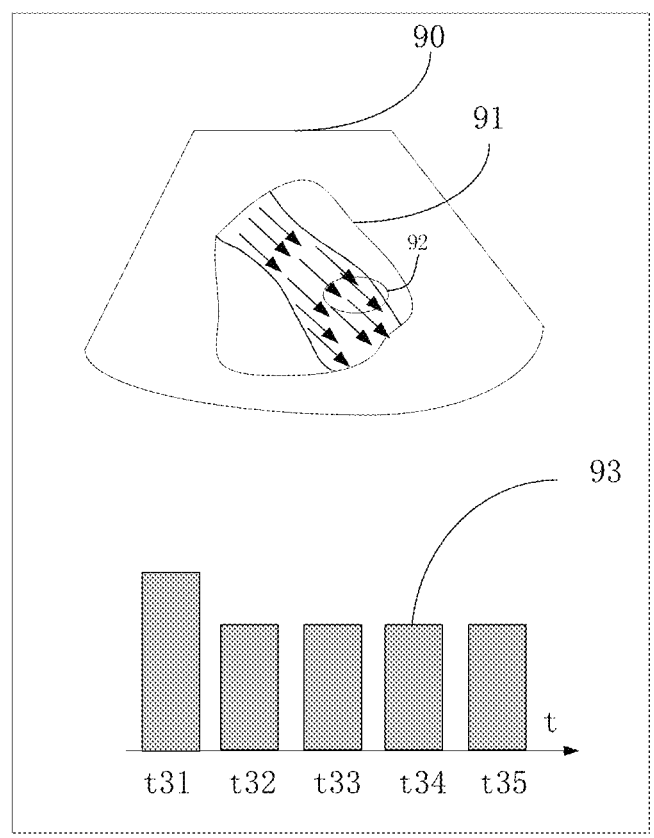

In addition, the icon model may also be constructed based on time change. For example, a coordinate representing the relationship between the dispersion and the time may be constructed to record the change of the quantification result of the dispersion with time. The change of the quantification results of dispersion with time may be displayed. The change of the quantification result of dispersion with time may be plotted in the coordinate to form a dispersion change diagram associated with the sampling box. The dispersion change diagram is one type of the icon model. Referring to FIG. 15, a display effect diagram is shown, in which the ultrasonic image 50 includes a large sampling box 51 and a small sampling box A32. The quantization results of dispersion corresponding to the small sampling box A32 are shown by diagram 53. The coordinate representing the relationship between the dispersion (e.g., the variance SD) and the time may be constructed, and the quantization results of dispersion at time t31, t32, t33, t34 and t35 may be obtained and plotted in the coordinate, thereby obtaining the dispersion change diagram shown by the diagram 53, which may be used to show the quantification result of dispersion in the small sampling box A32 at different times. In addition, the diagram 53 may also be marked with a black inverted triangle which indicating the position of the small sampling box A32 or indicating the position corresponding to the current time. In addition, FIG. 19 provides another display effect diagram in which the ultrasonic image 90 includes a large sampling box 91 and a small sampling box 92. The quantization results of dispersion corresponding to the small sampling box 92 are shown by the diagram 93. A time axis may be constructed, and the quantization results of dispersion at times t31, t32, t33, t34 and t35 may be plotted in the time axis. Rectangular columns corresponding to the times may be drawn on the time axis, where the color or height of each rectangular column may be related to the quantization result of dispersion corresponding to the current time, thereby forming the dispersion change diagram.

Regardless of which of the display modes above is used, the quantification result of the dispersion may be associated with the corresponding position range in the ultrasonic image. When the position range is changed, the quantification result may also be updated accordingly. For example, the sampling box may be used to mark the target point or the target point area of interest in the ultrasonic image. When the adjustment signal to the sampling box inputted by the user is obtained and the sampling box is redefined according to the adjustment signal, the multiple blood flow velocity directions associated with the redefined sampling box may be obtained in step S300. The meaning of being associated with the sampling box may include that the multiple blood flow velocity directions are selected in the sampling box or the number of the blood flow velocity directions is determined according to the number of the sampling boxes. When displaying the quantification results of the dispersion, the quantization results will change as the sampling box is updated. The change here may include that the number of quantification results and/or the value of the quantification result changes as the sampling box is updated.

The dispersion quantification results of the blood flow velocity directions may be displayed separately. Alternatively, they may be displayed together with the ultrasonic image on the display interface of the display. The ultrasonic image here may be one of a Doppler blood flow image, a blood flow projectile image and a B image, etc. That is, when displaying the quantification result of the dispersion, the ultrasonic image may be simultaneously displayed, and the blood flow velocity vectors may be superimposed on the ultrasonic image. A display method in which the blood flow velocity vectors are superimposed on the ultrasonic image will be provided below.

Figure 9A:
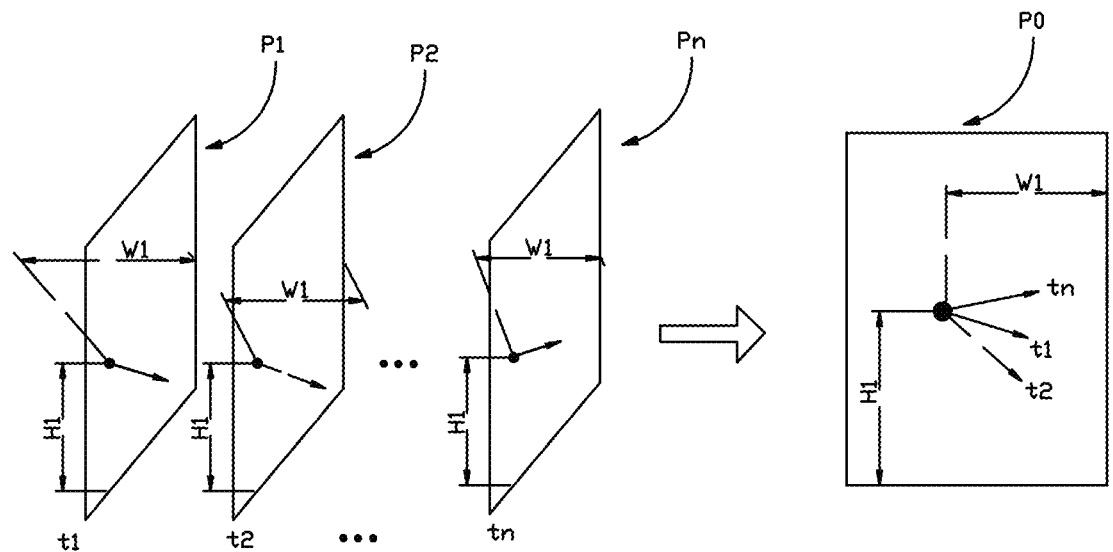
FIG. 9A is a schematic diagram of calculation of the blood flow velocity vector information in the first mode in one embodiment of the present disclosure.

In one embodiment, the step S200 may include calculating, according to the ultrasonic signal obtained in the step S100, a blood flow velocity vectors at a first display position in the ultrasonic images of the target point at different times to obtain the blood flow velocity vector information of the target point in the ultrasonic images at different times. In the following process, the blood flow velocity vector information at the first display position in the ultrasonic images at the times may be comparatively displayed. As shown in FIG. 9A, according to the ultrasonic signals obtained in the step S200 above, the ultrasonic image data P1, P2, . . . , Pn corresponding to the times t1, t2, . . . , to may be respectively obtained, and the blood flow velocity vectors of the target point at the first display position (the position of the black dot in the figure) in the ultrasonic images at the times may be calculated. In this embodiment, the first display position of the target point in the ultrasonic images at the times may be always located at the position (H1, W1) in the two-dimensional image. Based on this, when comparatively displaying the blood flow velocity vector information in subsequent step S800, the blood flow velocity vectors corresponding to the different times may be displayed at the target point (H1, W1) in the ultrasonic image P0 displayed by the display. In the case that all or a part of the target points are selected by the user or by the system by default as described in the embodiments above, the first display positions may be correspondingly obtained, and the blood flow velocity vector information at the first display position in the ultrasonic image corresponding to the current time may be calculated for comparative display. This display mode is referred to herein as the first mode in which the blood flow velocity vector is superimposed on the ultrasonic image. FIG. 9 (a) shows a display effect diagram of the two-dimensional image P0. This method may also be applied to three-dimensional image, that is, the ultrasonic image at the times may be the three-dimensional image database obtained by the scanning body above, and the first display position may be a spatial three-dimensional position in the three-dimensional image database, which will not be described again here.

In another embodiment, the step S200 may include calculating, according to the ultrasonic signals obtained in the step S100, the blood flow velocity vectors at the positions to which the target point is sequentially moved in the ultrasonic image, thereby obtaining the blood flow velocity vectors of the target points. In the present embodiment, the blood flow velocity vectors at the positions to which the target point is sequentially moved from an initial position in the ultrasonic image may be obtained by repeatedly calculating the blood flow velocity vector by which the target point is moved from one position to another position in the ultrasonic image in a time interval. That is, in the present embodiment, the calculation position for determining the blood flow velocity vector in the ultrasonic image may be obtained by calculation. Therefore, in the following process, what are comparatively displayed may be the blood flow velocity vectors at the positions obtained by calculation in the ultrasonic images at the times.

Figure 9B:
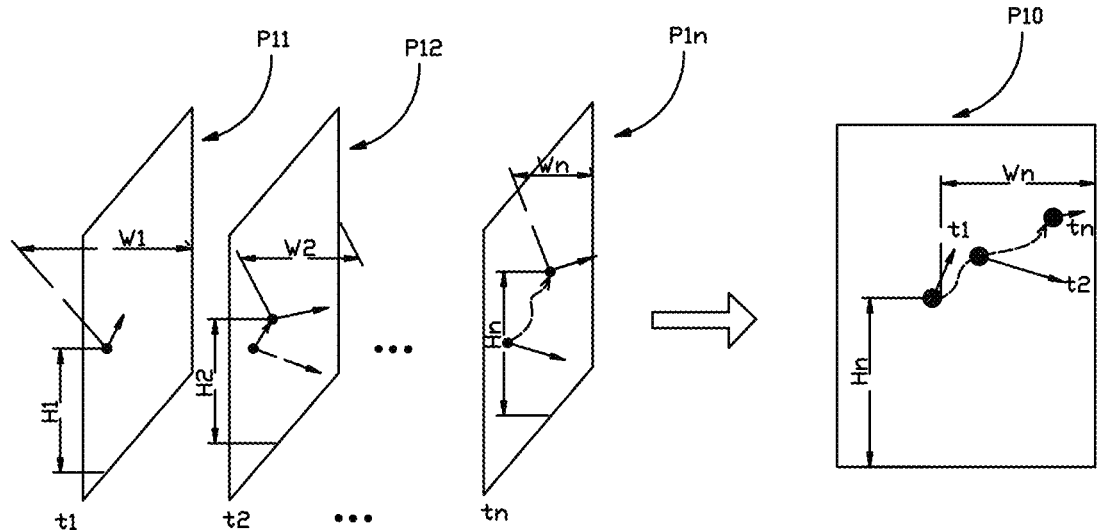
FIG. 9B is a schematic diagram of calculation of the blood flow velocity vector information in the second mode in one embodiment of the present disclosure.

As shown in FIG. 9B, the ultrasonic image data P11, P12 . . . P1n corresponding to the times t1, t2 . . . to may be respectively obtained according to the ultrasonic signals obtained in step S100. Thereafter, the initial position of the target point may be determined according to the part or all of the target points selected by the user or the density of target points determined by the system by default, etc. in the embodiment above, such as the first point (H1, W1) in FIG. 9B. And then, the blood flow velocity vector A1 at the initial position in the ultrasonic image P11 at the time t1 may be calculated. Next, the position (H2, W2) in the ultrasonic image P12 at the time t2 to which the target point (i.e., the black dot in the figure) is moved from the initial position in the ultrasonic image P11 at time t1 may be calculated, and the blood flow velocity vector at the position (H2, W2) in the ultrasonic image P12 may be obtained according to the ultrasonic signals for comparative display. For example, the displacement when reaching the second time t2 along the direction of the blood flow velocity vector at (H1, W1) in the ultrasonic image P11 at the time t1 in a time interval (the time interval=time t2−time t1) may be calculated, thereby obtaining the second display position of the target point at the first time t1 in the ultrasonic image at the second time. Thereafter, the blood flow velocity vector at this second display position may be obtained according to the ultrasonic signals obtained in the step S100 above, thereby obtaining the blood flow velocity vector information of the target point in the ultrasonic image P12 at the time t2, and so on. At each of two adjacent times, the displacement during the time interval between the two adjacent times along the direction of the blood flow velocity vector of the target point at the first time may be obtained, and the corresponding position of the target point in the ultrasonic image at the second time may be determined according to the displacement amount, and thereafter, the blood flow velocity vector at the position in the ultrasonic image at the second time to which the target point is moved from the first time may be obtained according to the ultrasonic signals. This way, the blood flow velocity vectors by which the target point is moved sequentially from (H1, w1) to (Hn, Wn) in the ultrasonic image may be obtained, thereby obtaining the blood flow velocity vectors at the positions in the ultrasonic images at different times to which the target point is sequentially moved from the initial position. Therefore, the blood flow velocity vectors of the target point may be obtained, which may be displayed simultaneously with the ultrasonic image.

In the display mode of the present embodiment, the displacement of the target point in a time interval may be calculated, and the corresponding position of the target point in the ultrasonic image may be determined according to the displacement. The movement may begin from an initially selected target point according to the time interval. The time interval may be determined by the transmission frequency of the system or by the display frame rate. Alternatively, the time interval may be a time interval inputted by the user. The position to which the target point will be moved may be calculated according to the time interval inputted by the user, and the blood flow velocity vector information at this position may be obtained for comparative display. Initially, N initial target points may be marked in the image using the ways described above. Each initial target point may have an arrow to indicate the magnitude and direction of the flow velocity at this point, as shown in FIG. 9B. In the process of displaying, the blood flow velocity vectors at the positions to which the target point is sequentially moved may be marked to form flowing markers which flow over time. By marking the blood flow velocity vectors obtained by the way as shown in FIG. 9B, the position of the arrow of each point will change in the newly generated image as time changes. This way, a flowing flow similar to the blood flow may be generated by the movement of the arrow, such that the user can observe the flow approximate to a true blood flow. This display mode is referred to herein as the second mode. Similarly, the effect diagram of the two-dimensional image P10 is shown in the example of FIG. 9B. It may also be applied to the three-dimensional image, that is, the ultrasonic images at the times may be the three-dimensional image database obtained by the scanning body above and the first display position may be a spatial three-dimensional position in the three-dimensional image database, which will not described again here.

In order to improve the display effect and prevent the human eye from being unrecognizable because the displayed blood flow velocity is too fast, in one embodiment, superimposing the blood flow velocity vector may further include slowing down the displaying of the blood flow velocity vector obtained in step S200. For example, the blood flow velocity vector may first be slowed down to obtain a slow blood flow velocity vector. And thereafter, the slow blood flow velocity vector may be superimposed on the ultrasonic image to form the blood flow projectile image, thereby achieving the comparative display of the blood flow velocity vector and the dispersion quantification results.

In one embodiment, particle projectile may be generated to show the change of the blood flow velocity at the target point. The coded color and/or length of the particle projectile may be associated with the blood flow velocity value at a particular location in the vessel. The particle projectile may be displayed on the display. The change of the particle projectile over time may be displayed on a specific position on the ultrasonic image to dynamically display the movement of the blood flow in the vessel by the dynamic display of the particle projectile, thereby obtaining the blood flow projectile image. Further, the particle projectile may further include a direction indicator whose direction is associated with the direction of the blood flow velocity. With the method of the present embodiment, the actual flowing state of the target point in the scan target may be clearly depicted in the displayed blood flow projectile image. Compared with the method of displaying the magnitude and direction of the blood flow velocity at the current position changed over time only at a corresponding display position in the image, the actual flowing state in the scan target may be displayed more precisely, more realistically and more vividly. Here, the flowing points or arrows, or other marks that can depict the direction may be used to present the flowing state of the blood flow. Referring to FIG. 15 to FIG. 19, the particle projectiles are arrows 83.

In addition, the particle projectile may also include only the direction indicator without carrying blood flow velocity value information. The direction of the direction indicator may be associated with the direction of blood flow velocity at a specific position in the scan target. The particle projectile including the direction indicator may be displayed at a specific position in the ultrasonic image to dynamically present the moving direction of the blood flow in the scan target.

In the present embodiment, the particle projectiles may be arrows. The length and/or thickness of the arrow may be used to represent the blood flow velocity value, and the direction of the arrow may be used to represent the direction of blood flow velocity. The specific position in this embodiment may mean that the blood flow velocity vector displayed at a specific position on the ultrasonic image corresponds to one particle projectile and the specific position may be a position used for marking the blood flow velocity value, e.g., the first display position or the second display position in FIG. 9A and FIG. 9B.

The multiple blood flow velocity directions used for calculating the dispersion may include the multiple blood flow velocity directions corresponding to any phase in the same cardiac cycle (e.g., systolic phase and/or diastolic phase) or the multiple blood flow velocity directions corresponding to the same phase (e.g., systolic phase or diastolic phase) in different cardiac cycles. When it is desired to select the blood flow velocity directions at multiple times in the cardiac cycle, reference may be made to the embodiment shown in FIG. 17. The ultrasonic image 70 may include a large sampling box 71 and a small sampling box 72. The small sampling box 72 may be used to select the position to be observed. The blood flow velocity directions corresponding to the frames at different times in the systole and/or diastolic phase may be selected by the cursor 73 based on the electrocardiogram or the Doppler spectrum image 74 provided on the display interface. Thereafter, the dispersion of the blood flow velocity directions in a systole phase or diastolic phase or in one cardiac cycle may be calculated. Therefore, in one embodiment, the graphic representing the cardiac cycle (including an electrocardiogram, a Doppler spectrogram, a video browsing axis including multiple frames of image of a cardiac cycle, and the like) may be displayed to visually determine the graphic at any time in the cardiac cycle. The selection signal of the user on the graphic representing the cardiac cycle may be obtained, and the multiple blood flow velocity directions corresponding to multiple times at the same position may be obtained according to the selection signal. In the present embodiment, the operation guide may be provided to the user very conveniently in the echocardiography mode.

FIG. 5 is a schematic flow chart of a parameter display method in an embodiment. It should be understood that although the various steps in the flowchart of FIG. 5 are sequentially displayed as indicated by the arrows, these steps are not necessarily performed in the order indicated by the arrows. Unless explicitly stated herein, the order of performance of these steps will not be strictly limited. They may be performed in other order. Moreover, at least a part of the steps in FIG. 5 may include multiple sub-steps or stages, which are not necessarily performed at the same time, but may be performed at different times. The sub-steps or stages will not be necessarily performed sequentially, but may be performed in parallel or alternately with other steps or at least a portion of the sub-steps or stages of the other steps. FIG. 10 to FIG. 12 show the extended embodiments of the embodiment in FIG. 5. Regarding the steps of the extended embodiments, reference may be made to the related descriptions above.

The various embodiments above have been described in the specific description only for the implementation of the corresponding steps. In the case of no logic conflict, the embodiments above may be combined with each other to form new technical solutions, which will be still within the scope of the present disclosure.

Through the description of the embodiments above, those skilled in the art can clearly understand that the method of foregoing embodiments may be implemented by software plus general hardware platform, or by hardware. Based on this understanding, the essential part or the part contributing to the prior art of the technical solution of the present disclosure may be embodied in the form of a software product carried on a non-transitory computer readable storage (e.g., a ROM, a disk, an optical disk, or a server cloud space). The software product may include instructions which may cause a terminal device (which may be a mobile phone, a computer, a server, or a network device, etc.) to perform the methods described in various embodiments of the present disclosure.

In the imaging method based on the blood flow velocity vector in the embodiments, the directions of the blood flow may be first calculated, and then be used to evaluate the degree of vortex or turbulence, thereby acting as a quantitative analysis method for judging the degree of stenosis. By calculating the variance of the blood flow directions at different positions at the same time or at the same positions at different times, the specific data used for diagnosis may be obtained, which provides a more intuitive image analysis result for the doctor and improves the intelligence of the ultrasonic imaging system.

The embodiments above have merely illustrated several implementations of the present disclosure, and the description thereof is relatively specific and detailed. However, it shall not be construed as limitation to the scope of the present disclosure. It should be noted that a number of changes and improvements may be made by those skilled in the art without departing from the spirit of the present disclosure, which shall all be within the scope of the present disclosure. Therefore, the protection scope of the present disclosure shall be determined by the appended claims.

I claim:

1. An ultrasonic blood flow parameter displaying method, comprising:
   obtaining an ultrasonic signal from a scan target through a probe;
   obtaining blood flow velocity vectors in the scan target according to the ultrasonic signal;
   obtaining an ultrasonic image of at least a portion of the scan target according to the ultrasonic signal;
   displaying the ultrasonic image;
   obtaining an indication of a sampling box on the ultrasonic image;
   extracting multiple blood flow velocity directions from the blood flow velocity vectors associated with the sampling box;
   calculating a variance or a standard deviation of the extracted multiple blood flow velocity directions;
   segmenting an area of the ultrasonic image associated with the sampling box into a plurality of non-overlapping regions according to the variance or the standard deviation for each region;
   constructing an icon model comprising a plurality of blocks respectively corresponding to the plurality of non-overlapping regions, wherein each block indicates the variance or the standard deviation of the extracted multiple blood flow velocity directions for the respective region; and
   comparatively displaying the icon model simultaneously with the ultrasonic image.

2. The method of claim 1, wherein extracting the multiple blood flow velocity directions from the blood flow velocity vectors comprises:
   calculating multiple unit vectors from the blood flow velocity vectors.

3. The method of claim 2, wherein calculating the variance of the extracted multiple blood flow velocity directions comprises:
   calculating an average in each dimension of the multiple unit vectors to obtain averages; and
   calculating the variance of the extracted multiple blood flow velocity directions according to the averages and the multiple unit vectors.

4. The method of claim 3, wherein calculating the variance of the extracted multiple blood flow velocity directions according to the averages and the multiple unit vectors comprises:
   calculating a quotient of a sum of squares of differences between a unit vector in each dimension of the multiple unit vectors and the average in said dimension divided by a number of the multiple unit vectors.

5. The method of claim 3, wherein calculating the standard deviation of the extracted multiple blood flow velocity directions comprises:
   calculating a square root of the calculated variance.

6. The method of claim 1, wherein the multiple blood flow velocity directions comprise at least one of:
   blood flow velocity directions at multiple positions at a same time; and
   multiple blood flow velocity directions at a same position at different times.

7. The method of claim 2, wherein obtaining the ultrasonic signal from the scan target through the probe and obtaining the blood flow velocity vectors in the scan target according to the ultrasonic signal comprises:
   obtaining ultrasonic signals in multiple different angles from the scan target by the probe, wherein the ultrasonic signals in the multiple different angles are in different receiving angles or different transmitting angles;
   storing the ultrasonic signals in different angles as at least two groups of data frame sets associated with the angles;
   calculating a blood flow velocity component corresponding to each group of data frame set according to the data frame set belonging to different angles to obtain at least two blood flow velocity components associated with the angles; and
   synthesizing the at least two blood flow velocity components to obtain the blood flow velocity vector.

8. The method of claim 7, wherein obtaining the ultrasonic signal from the scan target by the probe comprises:
   transmitting plane ultrasonic beams in different transmitting angles to the scan target through the probe; and
   receiving echoes of the plane ultrasonic beams to obtain plane ultrasonic signals in different transmitting angles which are used for calculating the blood flow velocity vector.

9. The method of claim 1, further comprising:
   generating an arrow when displaying the ultrasonic image, wherein at least one of a coded color andidr length of the arrow is associated with a blood flow velocity value at a specific position; and
   displaying the arrow at the specific position in the ultrasonic image to dynamically show a motion of a blood flow in the scan target.

10. The method of claim 1, further comprising:
    obtaining an ultrasonic image of at least a portion of the scan target according to the ultrasonic signal;
    generating a particle projectile comprising a direction indicator when displaying the ultrasonic image, wherein a direction of the direction indicator is associated with the blood flow velocity direction at a specific position in the scan target; and
    displaying the particle projectile at a specific position in the ultrasonic image to dynamically show a direction of motion of a blood flow in the scan target.

11. The method of claim 1, further comprising:
    obtaining an adjustment signal to the sampling box inputted by a user;
    determining a redefined sampling box according to the adjustment signal;
    extracting multiple blood flow velocity directions associated with the redefined sampling box;
    calculating an updated variance or an updated standard deviation of the extracted multiple blood flow velocity directions associated with the redefined sampling box; and
    changing the icon model such that each block indicates the updated variance or the updated standard deviation of the extracted multiple blood flow velocity directions for the respective region associated with the redefined sampling box.

12. The method of claim 1, before displaying the calculated variance or standard deviation, further comprising:
    recording a change of the calculated variance or standard deviation over time;
    wherein displaying the calculated variance or standard deviation comprises:
    displaying the change of the calculated variance or standard deviation over time to generate a change diagram associated with the sampling box.

13. The method of claim 1, wherein the extracted multiple blood flow velocity directions comprise:

multiple blood flow velocity directions corresponding to any phases in a same cardiac cycle; or multiple blood flow velocity directions corresponding a same phase in different cardiac cycles.

14. An ultrasonic imaging system, comprising:

a display;

a probe configured to transmit an ultrasonic beam to a scan target;

a receiving circuit configured to receive an echo signal of the ultrasonic beam;

a beam-former configured to perform a beam-forming on the echo signal to obtain an ultrasonic signal; and an image processor configured to:
  obtain blood flow velocity vectors in the scan target according to the ultrasonic signal;
  obtain an ultrasonic image of at least a portion of the scan target according to the ultrasonic signal;
  present the ultrasonic image on the display;
  obtain an indication of a sampling box on the ultrasonic image;
  extract multiple blood flow velocity directions from the blood flow velocity vectors associated with the sampling box;
  calculate a variance or a standard deviation of the extracted multiple blood flow velocity directions;
  segment an area of the ultrasonic image associated with the sampling box into a plurality of non-overlapping regions according to the variance or the standard deviation for each region; and
  construct an icon model comprising a plurality of blocks respectively corresponding to the plurality of non-overlapping regions, wherein each block indicates the variance or the standard deviation of the extracted multiple blood flow velocity directions for the respective region;

wherein the display is configured to comparatively present the icon model simultaneously with the ultrasonic image.

15. The ultrasonic imaging system of claim 14, wherein the image processor is configured to calculate multiple unit vectors from the blood flow velocity vectors.

16. The ultrasonic imaging system of claim 15, wherein the image processor is configured to calculate an average in each dimension of the multiple unit vectors to obtain averages and calculate the variance of the extracted multiple blood flow velocity directions according to the averages and the multiple unit vectors.

17. The ultrasonic imaging system of claim 16, wherein the image processor is configured to calculate a quotient of a sum of squares of differences between a unit vector in each dimension of the multiple unit vectors and the average in said dimension divided by a number of the multiple unit vectors.

18. The method of claim 1, wherein displaying the icon model comprises simultaneously displaying:

a text indication of the variance or the standard deviation;

a rectangular column including a color-coded portion that indicates a magnitude of the variance or the standard deviation; and a circular icon containing an arrow, wherein a direction of the arrow corresponds to a direction the extracted multiple blood flow velocity directions.

19. The ultrasonic imaging system of claim 14, wherein the image processor is further configured to simultaneously display with the icon model:

a text indication of the variance or the standard deviation;

a rectangular column including a color-coded portion that indicates a magnitude of the variance or the standard deviation; and a circular icon containing an arrow, wherein a direction of the arrow corresponds to a direction the extracted multiple blood flow velocity directions.

* * * * *